US012685486B2

(12) United States Patent
Bray et al.

(10) Patent No.: US 12,685,486 B2
(45) Date of Patent: Jul. 21, 2026

(54) SENSOR SHEET WITH DIGITAL DISTRIBUTED DATA ACQUISITION FOR WOUND MONITORING AND TREATMENT

(71) Applicant: Smith & Nephew PLC, Watford (GB)

(72) Inventors: David Michael Bray, Edinburgh (GB); Felix Clarence Quintanar, Hull (GB)

(73) Assignee: Smith & Nephew PLC, Watford (GB)

( * ) Notice: Subject to any disclaimer, the term of this patent is extended or adjusted under 35 U.S.C. 154(b) by 1187 days.

(21) Appl. No.: 17/626,089

(22) PCT Filed: Jul. 7, 2020

(86) PCT No.: PCT/EP2020/069080
§ 371 (c)(1),
(2) Date: Jan. 10, 2022

(87) PCT Pub. No.: WO2021/005036
PCT Pub. Date: Jan. 14, 2021

(65) Prior Publication Data
US 2022/0257851 A1 Aug. 18, 2022

(30) Foreign Application Priority Data
Jul. 11, 2019 (GB) ...................................... 1909947

(51) Int. Cl.
*A61B 5/00* (2006.01)
*A61B 5/01* (2006.01)
(Continued)

(52) U.S. Cl.
CPC .......... *A61B 5/6833* (2013.01); *A61B 5/0031* (2013.01); *A61B 5/0059* (2013.01);
(Continued)

(58) Field of Classification Search
CPC ... A61B 5/6833; A61B 5/0031; A61B 5/0059; A61B 5/01; A61B 5/026; A61B 5/053;
(Continued)

(56) References Cited

U.S. PATENT DOCUMENTS 3,896,802 A 7/1975 Williams
4,334,530 A 6/1982 Hassell
(Continued)

FOREIGN PATENT DOCUMENTS

CN 105232229 A 1/2016
CN 105395184 A 3/2016
(Continued)

OTHER PUBLICATIONS

Aubakir B., et al., "Vital Sign Monitoring Utilizing Eulerian Video Magnification and Thermography," 38th Annual International Conference of the IEEE Engineering in Medicine and Biology Society, Aug. 16, 2016, pp. 3527-3530 (4 pages).
(Continued)

*Primary Examiner* — Justin Xu
(74) *Attorney, Agent, or Firm* — Knobbe, Martens, Olson & Bear, LLP

(57) ABSTRACT

A wound monitoring and/or therapy apparatus can include multiple sensor circuits, a selection circuit coupled to each sensor circuit, and a processor configured to be in communication with the selection circuit. Each sensor circuit can process multiple sensor signals to generate a single output signal from the multiple sensor signals. Each of the sensor signals can correspond to a measurement of a sensor positioned on a substrate that is configured to be positioned at least partially in a wound. The selection circuit can receive the single output signals from the sensor circuits and outputs a selected single output signal. The processor can receive the selected single output signal and decomposes the selected (Continued)

signal output signal into the multiple sensor signals used to generate the selected single output signal. The processor can activate sensors and receive sensor data from the sensors. The processor can digitize the sensor data and transmit the digitized sensor data to a remote controller.

20 Claims, 8 Drawing Sheets

(51) Int. Cl.

| | |
|---|---|
| *A61B 5/026* | (2006.01) |
| *A61B 5/053* | (2021.01) |
| *A61B 5/11* | (2006.01) |
| *A61B 5/145* | (2006.01) |
| *A61B 5/1455* | (2006.01) |
| *A61B 5/318* | (2021.01) |
| *A61F 13/00* | (2024.01) |
| *A61F 13/05* | (2024.01) |
| *A61M 1/00* | (2006.01) |
| A61N 1/04 | (2006.01) |
| A61N 1/20 | (2006.01) |

(52) U.S. Cl.

CPC ................ *A61B 5/01* (2013.01); *A61B 5/026* (2013.01); *A61B 5/053* (2013.01); *A61B 5/11* (2013.01); *A61B 5/14542* (2013.01); *A61B 5/318* (2021.01); *A61F 13/00055* (2013.01); *A61F 13/00063* (2013.01); *A61F 13/05* (2024.01); *A61M 1/90* (2021.05); *A61M 1/95* (2021.05); *A61B 5/0008* (2013.01); *A61B 5/14539* (2013.01); *A61B 5/1455* (2013.01); *A61B 2562/0219* (2013.01); *A61B 2562/0247* (2013.01); *A61B 2562/066* (2013.01); *A61B 2562/164* (2013.01); *A61B 2562/166* (2013.01); *A61F 2013/00438* (2013.01); *A61F 2013/00953* (2013.01); *A61F 2013/00957* (2013.01); *A61F 2013/00961* (2013.01); *A61F 2013/0097* (2013.01); *A61M 2205/3306* (2013.01); *A61M 2205/3317* (2013.01); *A61M 2205/3324* (2013.01); *A61M 2205/3331* (2013.01); *A61M 2205/3368* (2013.01); *A61M 2205/50* (2013.01); *A61N 1/0468* (2013.01); *A61N 1/205* (2013.01)

(58) Field of Classification Search

CPC ....... A61B 5/11; A61B 5/14542; A61B 5/318; A61B 5/0008; A61B 5/14539; A61B 5/1455; A61B 2562/0219; A61B 2562/0247; A61B 2562/066; A61B 2562/164; A61B 2562/166; A61F 13/00055; A61F 13/00063; A61F 13/05; A61F 2013/00438; A61F 2013/00953; A61F 2013/00957; A61F 2013/00961; A61F 2013/0097; A61F 2013/0094; A61M 1/90; A61M 1/95; A61M 2205/3306; A61M 2205/3317; A61M 2205/3324; A61M 2205/3331; A61M 2205/3368; A61M 2205/50; A61N 1/0468; A61N 1/205

See application file for complete search history.

(56) References Cited

U.S. PATENT DOCUMENTS

| | | | |
|---|---|---|---|
| 5,090,410 A | 2/1992 | Saper et al. |
| 5,253,654 A | 10/1993 | Thomas et al. |
| 5,635,201 A | 6/1997 | Fabo |
| 5,642,096 A | 6/1997 | Leyerer et al. |
| 5,678,448 A | 10/1997 | Fullen et al. |
| 5,690,610 A | 11/1997 | Ito et al. |
| 5,836,990 A | 11/1998 | Li |
| 6,095,992 A | 8/2000 | Augustine |
| 6,178,342 B1 | 1/2001 | Borgos et al. |
| 6,381,482 B1 | 4/2002 | Jayaraman et al. |
| 6,517,484 B1 | 2/2003 | Wilk et al. |
| 6,551,252 B2 | 4/2003 | Sackner et al. |
| 6,731,987 B1 | 5/2004 | McAdams et al. |
| 7,077,832 B2 | 7/2006 | Fleischmann |
| 7,088,591 B2 | 8/2006 | Kishimoto et al. |
| 7,201,063 B2 | 4/2007 | Taylor |
| 7,206,623 B2 | 4/2007 | Blank et al. |
| 7,289,205 B2 | 10/2007 | Yaroslavsky et al. |
| 7,316,652 B2 | 1/2008 | Dalgaard et al. |
| 7,429,255 B2 | 9/2008 | Thompson |
| 7,520,875 B2 | 4/2009 | Bernabei |
| 7,521,292 B2 | 4/2009 | Rogers et al. |
| 7,569,742 B2 | 8/2009 | Haggstrom et al. |
| 7,625,117 B2 | 12/2009 | Haslett et al. |
| 7,687,678 B2 | 3/2010 | Jacobs |
| 7,846,141 B2 | 12/2010 | Weston |
| 7,877,866 B1 | 2/2011 | Greenberg et al. |
| 7,884,258 B2 | 2/2011 | Boehringer et al. |
| 7,904,133 B2 | 3/2011 | Gehman et al. |
| 7,922,676 B2 | 4/2011 | Daskal et al. |
| 7,942,869 B2 | 5/2011 | Houbolt et al. |
| 7,945,302 B2 | 5/2011 | McAdams |
| 8,019,401 B1 | 9/2011 | Smith et al. |
| 8,032,210 B2 | 10/2011 | Finneran et al. |
| 8,060,174 B2 | 11/2011 | Simpson et al. |
| 8,079,247 B2 | 12/2011 | Russell et al. |
| 8,111,165 B2 | 2/2012 | Ortega et al. |
| 8,116,841 B2 | 2/2012 | Bly et al. |
| 8,182,425 B2 | 5/2012 | Stamatas et al. |
| 8,238,996 B2 | 8/2012 | Burnes et al. |
| 8,241,231 B2 | 8/2012 | Bausewein et al. |
| 8,332,053 B1 | 12/2012 | Patterson et al. |
| 8,333,874 B2 | 12/2012 | Currie |
| 8,366,692 B2 | 2/2013 | Weston et al. |
| 8,480,641 B2 | 7/2013 | Jacobs |
| 8,525,340 B2 | 9/2013 | Eckhardt et al. |
| 8,579,872 B2 | 11/2013 | Coulthard et al. |
| 8,644,911 B1 | 2/2014 | Panasyuk et al. |
| 8,663,106 B2 | 3/2014 | Stivoric et al. |
| 8,682,442 B2 | 3/2014 | McAdams |
| 8,783,948 B2 | 7/2014 | Panda et al. |
| 8,788,009 B2 | 7/2014 | Greene et al. |
| 8,800,386 B2 | 8/2014 | Taylor |
| 8,818,478 B2 | 8/2014 | Scheffler et al. |
| 8,848,187 B2 | 9/2014 | Uematsu et al. |
| 8,894,590 B2 | 11/2014 | Lamoise et al. |
| 8,925,392 B2 | 1/2015 | Esposito et al. |
| 8,934,957 B2 | 1/2015 | Dias et al. |
| 8,934,965 B2 | 1/2015 | Rogers et al. |
| 8,943,897 B2 | 2/2015 | Beauvais et al. |
| 8,948,839 B1 | 2/2015 | Longinotti-Buitoni et al. |
| 8,997,588 B2 | 4/2015 | Taylor |
| 9,000,251 B2 | 4/2015 | Murphy et al. |
| 9,042,075 B2 | 5/2015 | Borini et al. |
| 9,192,531 B2 | 11/2015 | Wu |
| 9,220,455 B2 | 12/2015 | Sarrafzadeh et al. |
| 9,226,402 B2 | 12/2015 | Hsu |
| 9,282,897 B2 | 3/2016 | Ross, Jr. et al. |
| 9,314,175 B2 | 4/2016 | Jacofsky et al. |
| 9,320,473 B2 | 4/2016 | Shuler |
| 9,372,123 B2 | 6/2016 | Li et al. |
| 9,378,450 B1 | 6/2016 | Mei et al. |
| 9,380,698 B1 | 6/2016 | Li et al. |
| 9,386,947 B2 | 7/2016 | Johnson |
| 9,393,354 B2 | 7/2016 | Freedman et al. |
| 9,402,988 B2 | 8/2016 | Buchanan et al. |
| 9,408,573 B2 | 8/2016 | Welch et al. |
| 9,427,179 B2 | 8/2016 | Mestrovic et al. |
| 9,439,599 B2 | 9/2016 | Thompson et al. |
| 9,483,726 B2 | 11/2016 | Mei et al. |
| 9,494,474 B2 | 11/2016 | Servati et al. |

(56)     References Cited

U.S. PATENT DOCUMENTS

| | | |
|---|---|---|
| 9,511,215 B2 | 12/2016 | Skiba |
| 9,516,758 B2 | 12/2016 | Arora et al. |
| 9,526,439 B2 | 12/2016 | Connelly et al. |
| 9,554,484 B2 | 1/2017 | Rogers et al. |
| 9,572,507 B2 | 2/2017 | Moore et al. |
| 9,582,072 B2 | 2/2017 | Connor |
| 9,585,620 B2 | 3/2017 | Paquet et al. |
| 9,587,991 B2 | 3/2017 | Padiy |
| 9,592,007 B2 | 3/2017 | Nuovo et al. |
| 9,603,560 B2 | 3/2017 | Monty et al. |
| 9,610,388 B2 | 4/2017 | Aceto et al. |
| 9,613,911 B2 | 4/2017 | Rogers et al. |
| 9,629,584 B2 | 4/2017 | Macia et al. |
| 9,675,238 B2 | 6/2017 | Iida et al. |
| 9,687,195 B2 | 6/2017 | Sims et al. |
| 9,717,565 B2 | 8/2017 | Blair |
| 9,829,471 B2 | 11/2017 | Hammond et al. |
| 9,907,103 B2 | 2/2018 | Chen et al. |
| 9,999,711 B2 | 6/2018 | Weston et al. |
| 10,004,643 B2 | 6/2018 | Luckemeyer et al. |
| 10,046,096 B2 | 8/2018 | Askem et al. |
| 10,080,524 B1 | 9/2018 | Xi |
| 10,086,117 B2 | 10/2018 | Locke et al. |
| 10,117,705 B2 | 11/2018 | Chernov et al. |
| 10,152,789 B2 | 12/2018 | Carnes et al. |
| 10,166,387 B2 | 1/2019 | Bergelin et al. |
| 10,182,740 B2 | 1/2019 | Tonar et al. |
| 10,206,604 B2 | 2/2019 | Bergelin et al. |
| 10,207,031 B2 | 2/2019 | Toth |
| 10,209,213 B2 | 2/2019 | Kang et al. |
| 10,285,620 B2 | 5/2019 | Jung et al. |
| 10,321,862 B2 | 6/2019 | Dalene et al. |
| 10,463,773 B2 | 11/2019 | Haggstrom et al. |
| 10,687,984 B2 | 6/2020 | Rovaniemi |
| 10,702,153 B2 | 7/2020 | Shamim et al. |
| 10,716,490 B2 | 7/2020 | Connolly |
| 10,857,038 B2 | 12/2020 | Zamierowski et al. |
| 11,026,847 B2 | 6/2021 | Piotrowski et al. |
| 11,229,553 B2 | 1/2022 | Chen et al. |
| 11,647,922 B2 | 5/2023 | Scherer |
| 11,850,121 B2 | 12/2023 | Rapp |
| 2002/0016536 A1 | 2/2002 | Benni |
| 2002/0135752 A1 | 9/2002 | Sokolov et al. |
| 2003/0033032 A1 | 2/2003 | Lind et al. |
| 2003/0208148 A1 | 11/2003 | Sullivan |
| 2003/0210810 A1 | 11/2003 | Gee, Jr. et al. |
| 2003/0216630 A1 | 11/2003 | Jersey-Willuhn et al. |
| 2004/0230132 A1 | 11/2004 | Shehada |
| 2005/0088832 A1 | 4/2005 | Su et al. |
| 2005/0240107 A1 | 10/2005 | Alfano et al. |
| 2005/0280531 A1 | 12/2005 | Fadem et al. |
| 2006/0052678 A1 | 3/2006 | Drinan et al. |
| 2006/0058690 A1 | 3/2006 | Bartnik et al. |
| 2006/0173364 A1 | 8/2006 | Clancy et al. |
| 2006/0181791 A1 | 8/2006 | Van Beek et al. |
| 2006/0234383 A1 | 10/2006 | Gough |
| 2006/0241495 A1 | 10/2006 | Kurtz |
| 2007/0055209 A1 | 3/2007 | Patel et al. |
| 2007/0173892 A1 | 7/2007 | Fleischer et al. |
| 2007/0191754 A1 | 8/2007 | Aali |
| 2007/0260421 A1 | 11/2007 | Berner, Jr. et al. |
| 2007/0293748 A1 | 12/2007 | Engvall et al. |
| 2008/0081973 A1 | 4/2008 | Hoarau |
| 2008/0167535 A1 | 7/2008 | Stivoric et al. |
| 2008/0258717 A1 | 10/2008 | Igney et al. |
| 2008/0287747 A1 | 11/2008 | Mestrovic et al. |
| 2008/0319282 A1 | 12/2008 | Tran |
| 2008/0319283 A1 | 12/2008 | Cotton et al. |
| 2009/0149800 A1 | 6/2009 | Durand |
| 2009/0177051 A1 | 7/2009 | Arons et al. |
| 2009/0177110 A1 | 7/2009 | Lyden et al. |
| 2009/0209830 A1 | 8/2009 | Nagle et al. |
| 2009/0209896 A1 | 8/2009 | Selevan |
| 2009/0234206 A1 | 9/2009 | Gaspard et al. |
| 2009/0245601 A1 | 10/2009 | Cohen et al. |
| 2009/0253996 A1 | 10/2009 | Lee et al. |
| 2010/0022990 A1* | 1/2010 | Karpowicz ............. A61M 1/74 |
| | | 604/543 |
| 2010/0025831 A1 | 2/2010 | Yamazaki et al. |
| 2010/0166252 A1 | 7/2010 | Ahmed et al. |
| 2010/0168727 A1 | 7/2010 | Hancock et al. |
| 2010/0305473 A1 | 12/2010 | Yuzhakov |
| 2011/0004088 A1 | 1/2011 | Grossman |
| 2011/0015591 A1 | 1/2011 | Hanson et al. |
| 2011/0054283 A1 | 3/2011 | Shuler |
| 2011/0130697 A1 | 6/2011 | Nagle et al. |
| 2011/0140703 A1 | 6/2011 | Chiao et al. |
| 2011/0190639 A1 | 8/2011 | Peltie et al. |
| 2011/0218757 A1 | 9/2011 | Callsen et al. |
| 2011/0242532 A1 | 10/2011 | McKenna |
| 2011/0245682 A1 | 10/2011 | Robinson et al. |
| 2011/0301441 A1 | 12/2011 | Bandic et al. |
| 2012/0029306 A1 | 2/2012 | Paquet et al. |
| 2012/0029307 A1 | 2/2012 | Paquet et al. |
| 2012/0029410 A1 | 2/2012 | Koenig et al. |
| 2012/0165717 A1 | 6/2012 | Al Khaburi |
| 2012/0190989 A1 | 7/2012 | Kaiser et al. |
| 2012/0265120 A1 | 10/2012 | Beisang, III et al. |
| 2012/0271265 A1 | 10/2012 | Langdon |
| 2012/0277559 A1 | 11/2012 | Kohl-Bareis et al. |
| 2012/0316538 A1 | 12/2012 | Heiser et al. |
| 2012/0330252 A1 | 12/2012 | Stokes et al. |
| 2013/0041235 A1 | 2/2013 | Rogers et al. |
| 2013/0064772 A1 | 3/2013 | Swiss et al. |
| 2013/0121544 A1 | 5/2013 | Sarrafzadeh et al. |
| 2013/0123722 A1 | 5/2013 | Pratt et al. |
| 2013/0151223 A1 | 6/2013 | Zamierowski et al. |
| 2013/0200268 A1 | 8/2013 | Rafferty et al. |
| 2013/0261409 A1 | 10/2013 | Pathak et al. |
| 2013/0271278 A1 | 10/2013 | Duesterhoft et al. |
| 2013/0274563 A1 | 10/2013 | Duesterhoft et al. |
| 2013/0274629 A1 | 10/2013 | Duesterhoft et al. |
| 2013/0317367 A1 | 11/2013 | Shuler |
| 2014/0012108 A1 | 1/2014 | McPeak |
| 2014/0018637 A1 | 1/2014 | Bennett et al. |
| 2014/0024905 A1 | 1/2014 | Sarrafzadeh et al. |
| 2014/0031663 A1 | 1/2014 | Gallego et al. |
| 2014/0072190 A1 | 3/2014 | Wu et al. |
| 2014/0075658 A1 | 3/2014 | McGuin |
| 2014/0107495 A1 | 4/2014 | Marinelli et al. |
| 2014/0107498 A1 | 4/2014 | Bower et al. |
| 2014/0147611 A1 | 5/2014 | Ackerman, Jr. |
| 2014/0203797 A1 | 7/2014 | Stivoric et al. |
| 2014/0206947 A1 | 7/2014 | Isserow et al. |
| 2014/0232516 A1 | 8/2014 | Stivoric et al. |
| 2014/0235166 A1 | 8/2014 | Molettiere et al. |
| 2014/0243709 A1 | 8/2014 | Gibson et al. |
| 2014/0296749 A1 | 10/2014 | Reid, Jr. et al. |
| 2014/0298927 A1 | 10/2014 | Allin et al. |
| 2014/0298928 A1 | 10/2014 | Duesterhoft et al. |
| 2014/0303463 A1 | 10/2014 | Robinson et al. |
| 2014/0324120 A1 | 10/2014 | Bogie et al. |
| 2014/0340857 A1 | 11/2014 | Hsu et al. |
| 2014/0343478 A1 | 11/2014 | Brennan et al. |
| 2014/0350882 A1 | 11/2014 | Everett et al. |
| 2015/0018792 A1 | 1/2015 | Marsiquet et al. |
| 2015/0025343 A1 | 1/2015 | Gareau et al. |
| 2015/0138330 A1 | 5/2015 | Krishnamoorthi |
| 2015/0141767 A1 | 5/2015 | Rogers et al. |
| 2015/0148760 A1 | 5/2015 | Dodd et al. |
| 2015/0150479 A1 | 6/2015 | Yoshino et al. |
| 2015/0182166 A1 | 7/2015 | Evans et al. |
| 2015/0223716 A1 | 8/2015 | Korkala et al. |
| 2015/0257644 A1 | 9/2015 | Cao |
| 2015/0265191 A1 | 9/2015 | Harding et al. |
| 2015/0292968 A1 | 10/2015 | Vogt et al. |
| 2015/0313476 A1 | 11/2015 | Pisani et al. |
| 2015/0313533 A1 | 11/2015 | Rapp et al. |
| 2015/0327777 A1 | 11/2015 | Kostic et al. |
| 2015/0335254 A1 | 11/2015 | Fastert et al. |
| 2015/0335287 A1 | 11/2015 | Neuman et al. |
| 2015/0335288 A1 | 11/2015 | Toth et al. |
| 2015/0351970 A1 | 12/2015 | Dagger et al. |
| 2015/0359485 A1 | 12/2015 | Berg et al. |

(56) References Cited

U.S. PATENT DOCUMENTS

| | | |
|---|---|---|
| 2015/0374309 A1 | 12/2015 | Farkas et al. |
| 2016/0015962 A1 | 1/2016 | Shokoueinejad Maragheh et al. |
| 2016/0022223 A1 | 1/2016 | Grundfest et al. |
| 2016/0029900 A1 | 2/2016 | LaPlante et al. |
| 2016/0030132 A1 | 2/2016 | Cheung et al. |
| 2016/0038045 A1 | 2/2016 | Shapiro |
| 2016/0038083 A1 | 2/2016 | Ding et al. |
| 2016/0051147 A1 | 2/2016 | Cohen et al. |
| 2016/0058380 A1 | 3/2016 | Lee et al. |
| 2016/0066854 A1 | 3/2016 | Mei et al. |
| 2016/0069743 A1 | 3/2016 | McQuilkin et al. |
| 2016/0074234 A1 | 3/2016 | Abichandani et al. |
| 2016/0081601 A1 | 3/2016 | Ballam et al. |
| 2016/0100790 A1 | 4/2016 | Cantu et al. |
| 2016/0100987 A1 | 4/2016 | Hartwell et al. |
| 2016/0129469 A1 | 5/2016 | Kulinsky et al. |
| 2016/0143534 A1 | 5/2016 | Hyde et al. |
| 2016/0157779 A1 | 6/2016 | Baxi et al. |
| 2016/0213269 A1 | 7/2016 | Lam et al. |
| 2016/0228049 A1 | 8/2016 | Nackaerts et al. |
| 2016/0232807 A1 | 8/2016 | Ghaffari et al. |
| 2016/0242331 A1 | 8/2016 | Park et al. |
| 2016/0249810 A1 | 9/2016 | Darty et al. |
| 2016/0262672 A1 | 9/2016 | Hammond et al. |
| 2016/0262687 A1 | 9/2016 | Vaidyanathan et al. |
| 2016/0270700 A1 | 9/2016 | Baxi |
| 2016/0287177 A1 | 10/2016 | Huppert et al. |
| 2016/0302729 A1 | 10/2016 | Starr et al. |
| 2016/0310023 A1 | 10/2016 | Chachisvilis et al. |
| 2016/0317057 A1 | 11/2016 | Li et al. |
| 2016/0331263 A1 | 11/2016 | Cailler et al. |
| 2016/0331322 A1 | 11/2016 | Son et al. |
| 2016/0338591 A1 | 11/2016 | Lachenbruch et al. |
| 2016/0354001 A1 | 12/2016 | Buckley et al. |
| 2016/0367189 A1 | 12/2016 | Aimone et al. |
| 2016/0367192 A1 | 12/2016 | Iyengar et al. |
| 2016/0367406 A1 | 12/2016 | Barnett |
| 2017/0000407 A1 | 1/2017 | Saxby et al. |
| 2017/0007853 A1 | 1/2017 | Alford et al. |
| 2017/0027498 A1 | 2/2017 | Larson et al. |
| 2017/0079740 A1 | 3/2017 | Hufnagel et al. |
| 2017/0086519 A1 | 3/2017 | Vigano'et al. |
| 2017/0086709 A1 | 3/2017 | Khine et al. |
| 2017/0095208 A1 | 4/2017 | Oberleitner et al. |
| 2017/0146474 A1 | 5/2017 | Bedell et al. |
| 2017/0156594 A1 | 6/2017 | Stivoric et al. |
| 2017/0156621 A1 | 6/2017 | Bettinger et al. |
| 2017/0156658 A1 | 6/2017 | Maharbiz et al. |
| 2017/0164865 A1 | 6/2017 | Rafferty et al. |
| 2017/0164876 A1 | 6/2017 | Hyde et al. |
| 2017/0172439 A1 | 6/2017 | Zhu et al. |
| 2017/0202711 A1 | 7/2017 | Cernasov et al. |
| 2017/0224271 A1 | 8/2017 | Lachenbruch et al. |
| 2017/0231015 A1 | 8/2017 | Jang et al. |
| 2017/0258972 A1 | 9/2017 | Weston |
| 2017/0319075 A1 | 11/2017 | Homan et al. |
| 2017/0326004 A1 | 11/2017 | Long et al. |
| 2017/0367644 A1 | 12/2017 | Sharman et al. |
| 2018/0008177 A1 | 1/2018 | Shimuta et al. |
| 2018/0055697 A1 | 3/2018 | Mihali et al. |
| 2018/0056087 A1 | 3/2018 | Ribeiro et al. |
| 2018/0070880 A1 | 3/2018 | Trembly et al. |
| 2018/0074547 A1 | 3/2018 | Smadi et al. |
| 2018/0116877 A1 | 5/2018 | Ineichen |
| 2018/0132287 A1 | 5/2018 | Cheng et al. |
| 2018/0192514 A1 | 7/2018 | Seo |
| 2018/0200414 A1 | 7/2018 | Askem et al. |
| 2018/0206758 A1 | 7/2018 | Feldkamp et al. |
| 2018/0235484 A1 | 8/2018 | Mozdzierz |
| 2018/0296397 A1 | 10/2018 | Askem et al. |
| 2019/0021911 A1 | 1/2019 | Askem et al. |
| 2019/0060126 A1 | 2/2019 | Ribble et al. |
| 2019/0076298 A1 | 3/2019 | Quintanar et al. |
| 2019/0083025 A1 | 3/2019 | Aung et al. |
| 2019/0133812 A1 | 5/2019 | Seres et al. |
| 2019/0159938 A1 | 5/2019 | Askem et al. |
| 2019/0175098 A1 | 6/2019 | Burns |
| 2019/0192066 A1 | 6/2019 | Schoess et al. |
| 2019/0231939 A1 | 8/2019 | Askem et al. |
| 2019/0290496 A1 | 9/2019 | Brownhill et al. |
| 2019/0374387 A1 | 12/2019 | Ribble et al. |
| 2020/0054218 A1 | 2/2020 | Xi |
| 2020/0078482 A1 | 3/2020 | Yoon et al. |
| 2020/0078499 A1 | 3/2020 | Gadde et al. |
| 2020/0100711 A1 | 4/2020 | Choudhury et al. |
| 2020/0147407 A1 | 5/2020 | Efremkin |
| 2020/0281512 A1 | 9/2020 | Grubb et al. |
| 2020/0281513 A1 | 9/2020 | Grubb et al. |
| 2020/0281529 A1 | 9/2020 | Grubb et al. |
| 2020/0289346 A1 | 9/2020 | Hansen et al. |
| 2020/0330258 A1 | 10/2020 | Hansen et al. |
| 2020/0360547 A1 | 11/2020 | Smith et al. |
| 2021/0137446 A1 | 5/2021 | Brownhill et al. |
| 2021/0145359 A1 | 5/2021 | Hunt et al. |
| 2021/0212855 A1 | 7/2021 | Hansen et al. |

FOREIGN PATENT DOCUMENTS

| | | |
|---|---|---|
| CN | 106102322 A | 11/2016 |
| CN | 109350362 A | 2/2019 |
| DE | 102012211015 A1 | 1/2014 |
| DE | 102013013013 A1 | 2/2015 |
| EP | 1530034 A1 | 5/2005 |
| EP | 2454990 A2 | 5/2012 |
| EP | 2565630 A1 | 3/2013 |
| EP | 3034054 A1 | 6/2016 |
| EP | 3231478 A1 | 10/2017 |
| EP | 3409190 A1 | 12/2018 |
| EP | 3499510 A1 | 6/2019 |
| EP | 3837520 A1 | 6/2021 |
| EP | 4157178 A1 | 4/2023 |
| GB | 1476894 A | 6/1977 |
| GB | 2316171 A | 2/1998 |
| GB | 2563602 A | 12/2018 |
| JP | 2005046468 A | 2/2005 |
| JP | 2009225863 A | 10/2009 |
| KR | 20120119523 A | 10/2012 |
| KR | 101224629 B1 | 1/2013 |
| KR | 20140024743 A | 3/2014 |
| KR | 20140058041 A | 5/2014 |
| KR | 20160071044 A | 6/2016 |
| KR | 20190105898 A | 9/2019 |
| NL | 1027236 C2 | 4/2006 |
| WO | WO-9413197 A1 | 6/1994 |
| WO | WO-0021433 A1 | 4/2000 |
| WO | WO-0043046 A2 | 7/2000 |
| WO | WO-03067229 A1 | 8/2003 |
| WO | WO-2006041997 A2 | 4/2006 |
| WO | WO-2007030379 A2 | 3/2007 |
| WO | WO-2008006150 A1 | 1/2008 |
| WO | WO-2008010604 A1 | 1/2008 |
| WO | WO-2009052607 A1 | 4/2009 |
| WO | WO-2009120951 A2 | 10/2009 |
| WO | WO-2009141777 A1 | 11/2009 |
| WO | WO-2010020919 A1 | 2/2010 |
| WO | WO-2010105053 A2 | 9/2010 |
| WO | WO-2011082420 A1 | 7/2011 |
| WO | WO-2011123848 A1 | 10/2011 |
| WO | WO-2012106252 A1 | 8/2012 |
| WO | WO-2012141999 A1 | 10/2012 |
| WO | WO-2013026999 A1 | 2/2013 |
| WO | WO-2013044226 A2 | 3/2013 |
| WO | WO-2014036577 A1 | 3/2014 |
| WO | WO-2014116816 A1 | 7/2014 |
| WO | WO-2015112095 A1 | 7/2015 |
| WO | WO-2015168720 A1 | 11/2015 |
| WO | WO-2016025438 A1 | 2/2016 |
| WO | WO-2016030752 A1 | 3/2016 |
| WO | WO-2016058032 A1 | 4/2016 |
| WO | WO-2016073777 A1 | 5/2016 |
| WO | WO-2016100218 A1 | 6/2016 |
| WO | WO-2016110564 A1 | 7/2016 |
| WO | WO-2016187136 A1 | 11/2016 |
| WO | WO-2016205872 A1 | 12/2016 |

(56) References Cited

FOREIGN PATENT DOCUMENTS

| WO | WO-2016205881 A1 | 12/2016 |
| WO | WO-2017021006 A1 | 2/2017 |
| WO | WO-2017021965 A2 | 2/2017 |
| WO | WO-2017033058 A1 | 3/2017 |
| WO | WO-2017037479 A1 | 3/2017 |
| WO | WO-2017041014 A1 | 3/2017 |
| WO | WO-2017041385 A1 | 3/2017 |
| WO | WO-2017041386 A1 | 3/2017 |
| WO | WO-2017041387 A1 | 3/2017 |
| WO | WO-2017119996 A1 | 7/2017 |
| WO | WO-2017205728 A1 | 11/2017 |
| WO | WO-2017214188 A1 | 12/2017 |
| WO | WO-2018035612 A1 | 3/2018 |
| WO | WO-2018060417 A1 | 4/2018 |
| WO | WO-2018064569 A1 | 4/2018 |
| WO | WO-2018115461 A1 | 6/2018 |
| WO | WO-2018144938 A1 | 8/2018 |
| WO | WO-2018144941 A1 | 8/2018 |
| WO | WO-2018144943 A1 | 8/2018 |
| WO | WO-2018144946 A1 | 8/2018 |
| WO | WO-2018185138 A1 | 10/2018 |
| WO | WO-2018189265 A1 | 10/2018 |
| WO | WO-2018209090 A1 | 11/2018 |
| WO | WO-2018211458 A1 | 11/2018 |
| WO | WO-2018234443 A1 | 12/2018 |
| WO | WO-2019020550 A2 | 1/2019 |
| WO | WO-2019020551 A1 | 1/2019 |
| WO | WO-2019020666 A1 | 1/2019 |
| WO | WO-2019030384 A2 | 2/2019 |
| WO | WO-2019048624 A1 | 3/2019 |
| WO | WO-2019048626 A1 | 3/2019 |
| WO | WO-2019048638 A1 | 3/2019 |
| WO | WO-2019063481 A1 | 4/2019 |
| WO | WO-2019063488 A2 | 4/2019 |
| WO | WO-2019067264 A1 | 4/2019 |
| WO | WO-2019072531 A1 | 4/2019 |
| WO | WO-2019076967 A2 | 4/2019 |
| WO | WO-2019096828 A1 | 5/2019 |
| WO | WO-2019140441 A2 | 7/2019 |
| WO | WO-2019140444 A1 | 7/2019 |
| WO | WO-2019140448 A1 | 7/2019 |
| WO | WO-2019140449 A1 | 7/2019 |
| WO | WO-2019193141 A1 | 10/2019 |
| WO | WO-2019216883 A1 | 11/2019 |
| WO | WO-2019230183 A1 | 12/2019 |
| WO | WO-2019238180 A1 | 12/2019 |
| WO | WO-2019238181 A1 | 12/2019 |
| WO | WO-2019238182 A1 | 12/2019 |
| WO | WO-2019238195 A1 | 12/2019 |
| WO | WO-2019238196 A1 | 12/2019 |
| WO | WO-2019238197 A1 | 12/2019 |
| WO | WO-2019238198 A1 | 12/2019 |
| WO | WO-2020002416 A1 | 1/2020 |
| WO | WO-2020043806 A1 | 3/2020 |
| WO | WO-2020139541 A1 | 7/2020 |
| WO | WO-2020157103 A1 | 8/2020 |
| WO | WO-2020159677 A1 | 8/2020 |
| WO | WO-2020167547 A1 | 8/2020 |
| WO | WO-2020242876 A1 | 12/2020 |
| WO | WO-2021059209 A1 | 4/2021 |
| WO | WO-2021250494 A1 | 12/2021 |

OTHER PUBLICATIONS

Bandodkar A.J., et al., "Battery-Free, Skin-Interfaced Microfluidic/ Electronic Systems for Simultaneous Electrochemical, Colorimetric and Volumetric Analysis of Sweat," Science Advances, vol. 5 (1), Jan. 18, 2019, retrieved from http://advances.sciencemag.org/content/ 5/1/eaav3294, 16 pages.

Cauwe M., et al., "Technology Development for a Low-Cost, Roll-to-Roll Chip Embedding Solution Based on PET Foils," 18th European Microelectronics and Packaging Conference (EMPC), IEEE, Sep. 12, 2011, 6 pages.

Farooqui M.F., et al., "Low Cost Inkjet Printed Smart Bandage for Wireless Monitoring of Chronic Wounds," Scientific Reports, vol. 6, Jun. 29, 2016, 14 pages.

Geng Y., et al., "A Hybrid Low Power Biopatch for Body Surface Potential Measurement," IEEE Journal of Biomedical and Health Informatics, vol. 17, No. 3, May 1, 2013, pp. 591-599.

George J., et al., "Reliability of Plastic-Encapsulated Electronic Components in Supersaturated Steam Environments," IEEE Transactions on Components, Packaging and Manufacturing Technology, vol. 5 (10), Oct. 2015, pp. 1423-1431.

Iannetta Jr. R.A., et al., "Successful Case Histories of Polymer Based Circuitry on Flexible Film Substrates," Electro/94 International Conference Proceedings Combined vols. IEEE, XP010149465, May 10-12, 1994, pp. 885-889.

International Search Report and Written Opinion for Application No. PCT/EP2020/069080, mailed on Dec. 1, 2020, 19 pages.

Little Miss Plasters, kidstravelclub.co.uk., retrieved from http:// www.kidstravelclub.co.uk/little-miss-girls-childrens-plasters on Aug. 26, 2016, 2 pages.

Lu B., et al., "A Study of the Autofluorescence of Parylene Materials for uTAS Applications," Lab on Chip, vol. 10 (14), Jul. 2010, pp. 1826-1834.

Mcleod A.J., et al., "Motion Magnification for Endoscopic Surgery," Progress in Biomedical Optics and Imaging, SPIE— International Society for Optical Engineering, Mar. 12, 2014, vol. 9036, 8 pages.

Mehmood N., et al., "Applications of Modern Sensors And Wireless Technology In Effective Wound Management: Modern Sensors And Wireless Technology," Journal of Biomedical Materials Research Part B, vol. 102, May 1, 2014, XP055739544, pp. 885-895.

Mostafalu P., et al., "Wireless Flexible Smart Bandage for Continuous Monitoring Of Wound Oxygenation," IEEE Transactions on Biomedical Circuits and Systems, vol. 9 (5), Oct. 1, 2015, XP055526132, pp. 670-677 (8 pages).

Narusawa H., "The Corona Discharge Causes Short Destruction that had Bad Influence on a Power Switching Circuit," Adphox Corporation, Jan. 1, 2009, retrieved from http://www.adphox.co.jp/keisokuki/ ke-english-corona/CORONA_DISCHARGE_EN.pdf, 12 pages.

Pang Q., et al., "Smart Flexible Electronics-Integrated Wound Dressing for Real-Time Monitoring and On-Demand Treatment of Infected Wounds," Advanced Science, vol. 7, No. 6, Mar. 2020, 1902673, XP055739532, 10 pages.

Raviglione A., et al., "Real-Time Smart Textile-Based System to Monitor Pressure Offloading of Diabetic Foot Ulcers," Journal of Diabetes Science and Technology, vol. 11 (5), Sep. 2017, pp. 894-898.

Rose D.P., et al., "Adhesive RFID Sensor Patch for Monitoring of Sweat Electrolytes," IEEE Transactions on Biomedical Engineering, vol. 62 (6), Jun. 2015, first published on Nov. 11, 2015, pp. 1457-1465.

Wakita J., et al., "Variations in Optical Absorption and Fluorescence Spectra for Polyimide Thin Films Caused by Structural Isomerism," Journal of Photopolymer Science and Technology, Jan. 1, 2003, 1 page.

Willis B., "Conformal Coating Inspection & Coating Faults," Vision Engineering, Jul. 21, 2016, retrieved from http://www.visioneng. com/wp-content/uploads/2017/11/Conformal-Coating-Inspection- and-Defects.21JUL16.pdf, 35 pages.

Willis B., "Guide to Conformal Coating & Cleaning Defects Contents," Mar. 1, 2014, retrieved from http://coatingguide.smartgroup. org/Files%20pdf/Coating%20Defects%20V2%2014March2014. pdf, vol. 1, 31 pages.

International Preliminary Report on Patentability for Application No. PCT/EP2020/069080, mailed on Jan. 20, 2022, 11 pages.

* cited by examiner

140

202 →

SENSOR SHEET WITH DIGITAL DISTRIBUTED DATA ACQUISITION FOR WOUND MONITORING AND TREATMENT

CROSS-REFERENCE TO RELATED APPLICATIONS

This application is a U.S. national stage application of International Patent Application No. PCT/EP2020/069080, filed Jul. 7, 2020, which claims priority to U.K. Patent Application No. 1909947.2, filed on Jul. 11, 2019, entitled "SENSOR SHEET WITH DIGITAL DISTRIBUTED DATA ACQUISITION FOR WOUND MONITORING AND TREATMENT," the disclosure of each of which is hereby incorporated by reference in its entirety.

FIELD

Embodiments of the present disclosure relate to sensor integrated substrates, which can be incorporated into wound dressings and systems, and in particular to design rules for such substrates.

BACKGROUND

Nearly all areas of medicine may benefit from improved information regarding the state of the tissue, organ, or system to be treated, particularly if such information is gathered in real-time during treatment. Many types of treatments are still routinely performed without the use of sensor data collection; instead, such treatments rely upon visual inspection by a caregiver or other limited means rather than quantitative sensor data. For example, in the case of wound treatment via dressings and/or negative pressure wound therapy, data collection is generally limited to visual inspection by a caregiver and often the underlying wounded tissue may be obscured by bandages or other visual impediments. Even intact, unwounded skin may have underlying damage that is not visible to the naked eye, such as a compromised vascular or deeper tissue damage that may lead to an ulcer. Similar to wound treatment, during orthopedic treatments requiring the immobilization of a limb with a cast or other encasement, only limited information is gathered on the underlying tissue. In instances of internal tissue repair, such as a bone plate, continued direct sensor-driven data collection is not performed. Further, braces and/or sleeves used to support musculoskeletal function do not monitor the functions of the underlying muscles or the movement of the limbs. Outside of direct treatments, common hospital room items such as beds and blankets could be improved by adding capability to monitor patient parameters.

Such wound monitoring and/or treatment systems present unique problems due to being in contact with tissue. In addition, a wound should be allowed to heal without impediment. At the same time, care must be taken to ensure that such systems are reliable and safe for use on human or animal tissue.

Therefore, there is a need for improved wound monitoring and/or treatment systems.

SUMMARY

A wound monitoring and/or therapy apparatus can include a plurality of sensor circuits. Each sensor circuit can be configured to process a plurality of input signals to generate a single output signal from the plurality of input signals. Each of the plurality of input signals can correspond to a measurement of a different sensor of a plurality of sensors positioned on a substrate. The wound monitoring and/or therapy apparatus can include a selection circuit coupled to each sensor circuit. The selection circuit can be configured to receive the plurality of single output signals from the plurality of sensor circuits and output the single output signal of a selected sensor circuit of the plurality of sensor circuits. The wound monitoring and/or therapy apparatus can include a processor configured to be in electrical communication with the selection circuit. The processor can be configured to communicate, to the selection circuit, which of the plurality of sensor circuits to select; receive, from the selection circuit, the single output signal of the selected sensor circuit; and separately extract each of the plurality of input signals from the single output signal of the selected sensor circuit. The substrate can be configured to be positioned at least partially in a wound. The substrate can support at least one of the plurality of sensors or the selection circuit.

The wound monitoring and/or therapy apparatus of any of the preceding paragraphs and/or any of the apparatuses and/or systems disclosed herein may include any combination of the following features described in this paragraph, among other features described herein. The plurality of input signals can include a first input signal and a second input signal. The first input signal can correspond to a zero-frequency component of the single output signal. The second input signal can correspond to a non-zero-frequency component of the single output signal. The non-zero-frequency component of the single output signal can be a first non-zero-frequency component of the single output signal, and the plurality of input signals can include a third input signal. The third input signal can correspond to a second non-zero-frequency component of the single output signal that is different from the first non-zero-frequency component of the single output signal. The first non-zero-frequency component of the single output signal can correspond to a frequency of approximately 50 kHz. The second non-zero-frequency component of the single output signal can correspond to a frequency between approximately 1 kHz and approximately 10 kHz.

The wound monitoring and/or therapy apparatus of any of the preceding paragraphs and/or any of the apparatuses and/or systems disclosed herein may include any combination of the following features described in this paragraph, among other features described herein. The plurality of input signals can include a first input signal and a second input signal. The first input signal can correspond to a DC component of the single output signal. The first input signal can correspond to measurement from a first sensor of the plurality of sensors. The second input signal can correspond to a measurement from a second sensor of the plurality of sensors. Each of the first and second sensors can include one of a temperature sensor, an optical sensor, an accelerometer, a motion sensor, a gyroscope, an impedance sensor, a conductivity sensor, a pH sensor, a pressure sensor, or a perfusion sensor. The first and second sensors can be the same or different. The first sensor can be a temperature sensor and the second sensor can be an impedance sensor.

The wound monitoring and/or therapy apparatus of any of the preceding paragraphs and/or any of the apparatuses and/or systems disclosed herein may include any combination of the following features described in this paragraph, among other features described herein. The processor can be configured to separately extract each of the plurality of input signals from the single output signal of the selected sensor circuit by being configured to: determine a first input signal of the plurality of input signals based at least in part on a zero-frequency component of the single output signal of the selected sensor circuit; and determine a second input signal of the plurality of input signals based at least in part on a non-zero-frequency component of the single output signal of the selected sensor circuit. The wound monitoring and/or therapy apparatus can include at least one of the substrate or the plurality of sensors positioned on the substrate.

A wound monitoring and/or therapy system can include a substrate configured to be positioned at least partially in a wound; at least one first sensor of a first sensor type positioned on the substrate; and at least one second sensor of a second sensor type positioned on the substrate. The second sensor type can be different from the first sensor type. The wound monitoring and/or therapy system can include a processor in electrical communication with the first and second sensors. The processor can be positioned on the substrate. The processor can be configured to receive, over a wired interface, control commands from a controller that can be external to the substrate. The processor can be configured to activate at least one of the at least one first sensor or at least one second sensor based at least in part on the control commands. The processor can be configured to digitize sensor data received from at least one of the at least one first sensor or at least one second sensor. The processor can be configured to transmit to the controller, over the wired interface, the digitized sensor data of at least one of the first or second sensor data.

The system of any of the preceding paragraphs and/or any of the apparatuses and/or systems disclosed herein may also include any combination of the following features described in this paragraph, among other features described herein. Each of the at least of the at last one first sensor or the at least one second sensor can include a temperature sensor, an optical sensor, an accelerometer, a motion sensor, a gyroscope, an impedance sensor, a conductivity sensor, a pH sensor, a pressure sensor, or a perfusion sensor. The first and second sensors can be the same or different. The at least one first sensor can include a plurality of temperature sensors. The at least one second sensor can include a plurality of optical sensors.

The system of any of the preceding paragraphs and/or any of the apparatuses and/or systems disclosed herein may include any combination of the following features described in this paragraph, among other features described herein. Each temperature sensor of the plurality of temperature sensors can produce analog sensor data. Each temperature sensor can be connected to a respective analog sensor input of the processor. Each optical sensor of the plurality of optical sensors can produce digital sensor data. Each optical sensor can be connected to a respective digital signal input of the processor. Each optical sensor of the plurality of optical sensors can produce digital sensor data. Each optical sensor can be connected to a respective digital signal input of the processor. The processor can be configured to communicate with the controller using a serial protocol. The serial protocol can be Inter-integrated Circuit (I2C) Protocol.

A monitoring and/or therapy system can include a substrate configured to be positioned at least partially in a wound and a plurality of sensors positioned on the substrate. The sensors can be configured to detect physiological data associated with the wound. The system can include a plurality of light sources positioned on the substrate; and a control circuit positioned on the substrate. The control circuit can be configured to receive data from at least some sensors of the plurality of sensors; and control the light sources to communicate the received data to a remote computing device via an optical communication protocol.

The system of any of the preceding paragraphs and/or any of the systems and/or apparatuses disclosed herein may include any combination of the following features described in this paragraph, among other features described herein. The light sources can be positioned in at least one of at an edge or in a corner of the substrate. The substrate can include a plurality of perforations. The light sources can be positioned in an area of the substrate that does not include perforations. The light sources can be positioned in an area of the substrate that includes perforations with density below a threshold. The substrate can be coated with a substantially optically transparent coating.

The system of any of the preceding paragraphs and/or any of the systems and/or apparatuses disclosed herein may include any combination of the following features described in this paragraph, among other features described herein. The system can include a remote computing device that can include an external controller. The system can include a plurality of light detectors positioned on the substrate. The control circuit can be configured to receive, from the light detectors, data transmitted by the remote computing device via the optical communication protocol.

In some cases, a wound monitoring and/or therapy apparatus (such as a wound dressing) manufactured using the methods of any one or more of preceding paragraphs and/or any of the methods described herein is disclosed. In some cases, a substrate supporting one or more electronic components and/or connections manufactured using the methods of any one or more of preceding paragraphs and/or any of the methods described herein is disclosed. Disclosed are methods of operating any of the wound monitoring and/or therapy apparatuses and/or systems disclosed herein.

BRIEF DESCRIPTION OF THE DRAWINGS

Embodiments of the present disclosure will now be described hereinafter, by way of example only, with reference to the accompanying drawings in which.

DETAILED DESCRIPTION

Figure 1A:
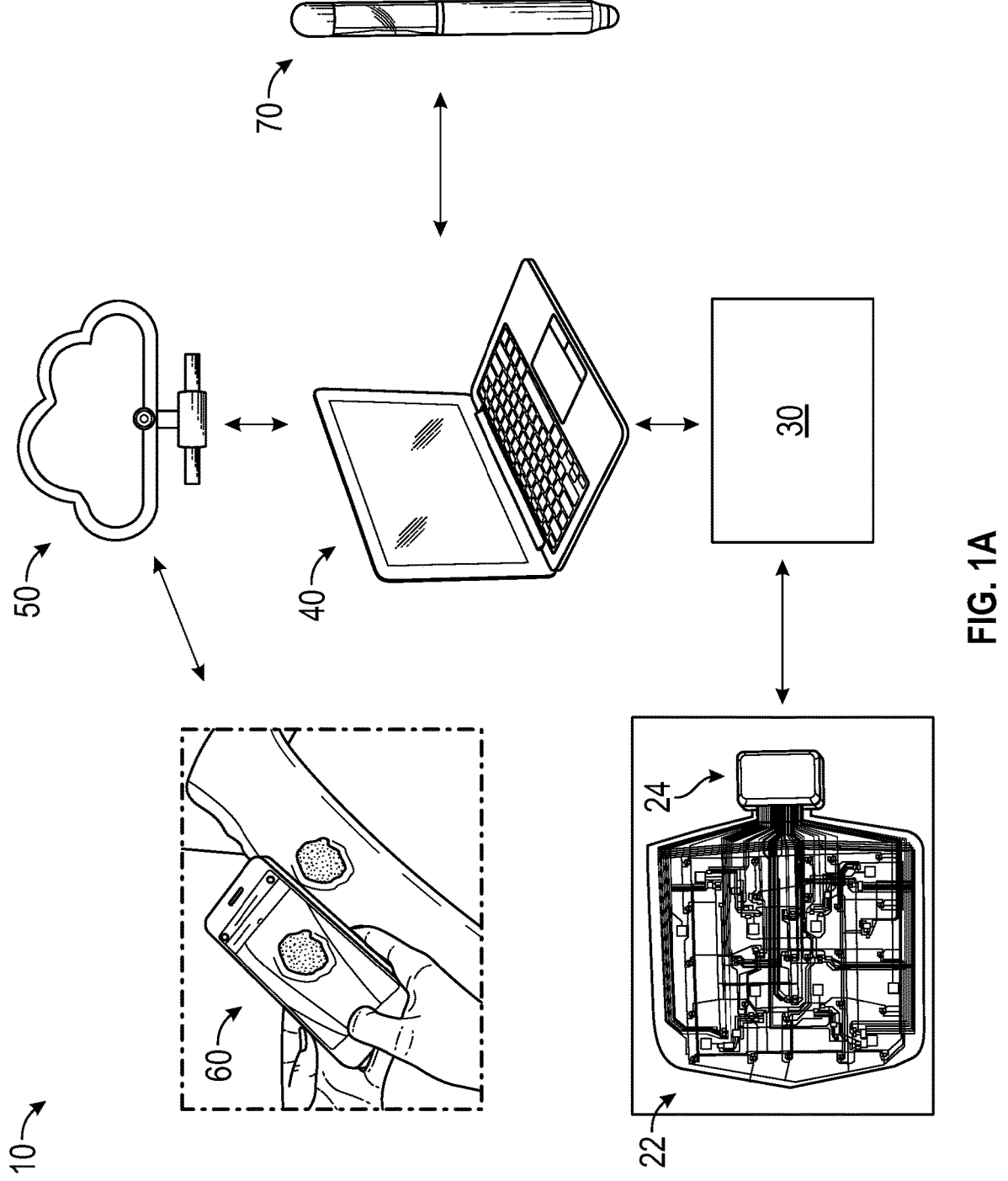
FIG. 1A illustrates a wound monitoring or therapy system.

Embodiments disclosed herein relate to apparatuses and methods of at least one of monitoring or treating biological tissue with sensor-enabled substrates. The systems and methods disclosed herein are not limited to treatment or monitoring of a particular type of tissue or injury, instead the sensor-enabled technologies disclosed herein are broadly applicable to any type of therapy that may benefit from sensor-enabled substrates. Some implementations utilize sensors and data collection relied upon by health care providers to make both diagnostic and patient management decisions.

Some systems and methods disclosed herein relate to the use of sensors mounted on or embedded within substrates configured to be used in the treatment of both intact and damaged human or animal tissue. Such sensors may collect information about the surrounding tissue and transmit such information to a computing device or a caregiver to be utilized in further treatment. In certain cases, such sensors may be attached to the skin anywhere on the body, including areas for monitoring arthritis, temperature, or other areas that may be prone to problems and require monitoring. Sensors disclosed herein may also incorporate markers, such as radiopaque markers, to indicate the presence of the device, for example prior to performing an MRI or other technique.

The sensor systems and methods disclosed herein may be used in combination with clothing. Non-limiting examples of clothing for use with the sensor systems and methods disclosed herein include shirts, pants, trousers, dresses, undergarments, outer-garments, gloves, shoes, hats, and other suitable garments. In certain cases, the sensor systems and methods disclosed herein may be welded into or laminated into/onto the particular garments. The sensor systems and methods may be printed directly onto the garment and/or embedded into the fabric. Breathable and printable materials such as microporous membranes may also be suitable.

Sensor systems and methods disclosed herein may be incorporated into cushioning or bed padding, such as within a hospital bed, to monitor patient characteristics, such as any characteristic disclosed herein. In certain cases, a disposable film containing such sensors could be placed over the hospital bedding and removed/replaced as needed.

In some implementations, the sensor systems and methods disclosed herein may incorporate energy harvesting, such that the sensor systems and methods are self-sustaining. For example, energy may be harvested from thermal energy sources, kinetic energy sources, chemical gradients, or any suitable energy source.

The sensor systems and methods disclosed herein may be utilized in rehabilitation devices and treatments, including sports medicine. For example, the sensor systems and methods disclosed herein may be used in braces, sleeves, wraps, supports, and other suitable items. Similarly, the sensor systems and methods disclosed herein may be incorporated into sporting equipment, such as helmets, sleeves, and/or pads. For example, such sensor systems and methods may be incorporated into a protective helmet to monitor characteristics such as acceleration, which may be useful in concussion diagnosis.

The sensor systems and methods disclosed herein may be used in coordination with surgical devices, for example, the NAVIO surgical system by Smith & Nephew Inc. In some implementations, the sensor systems and methods disclosed herein may be in communication with such surgical devices to guide placement of the surgical devices. In some implementations, the sensor systems and methods disclosed herein may monitor blood flow to or away from the potential surgical site or ensure that there is no blood flow to a surgical site. Further surgical data may be collected to aid in the prevention of scarring and monitor areas away from the impacted area.

To further aid in surgical techniques, the sensors disclosed herein may be incorporated into a surgical drape to provide information regarding tissue under the drape that may not be immediately visible to the naked eye. For example, a sensor embedded flexible drape may have sensors positioned advantageously to provide improved area-focused data collection. In certain implementations, the sensor systems and methods disclosed herein may be incorporated into the border or interior of a drape to create fencing to limit/control the surgical theater.

Sensor systems and methods disclosed herein may also be utilized for pre-surgical assessment. For example, such sensor systems and methods may be used to collect information about a potential surgical site, such as by monitoring skin and the underlying tissues for a possible incision site. For example, perfusion levels or other suitable characteristics may be monitored at the surface of the skin and deeper in the tissue to assess whether an individual patient may be at risk for surgical complications. Sensor systems and methods such as those disclosed herein may be used to evaluate the presence of microbial infection and provide an indication for the use of antimicrobials. Further, sensor systems and methods disclosed herein may collect further information in deeper tissue, such as identifying pressure ulcer damage and/or the fatty tissue levels.

The sensor systems and methods disclosed herein may be utilized in cardiovascular monitoring. For example, such sensor systems and methods may be incorporated into a flexible cardiovascular monitor that may be placed against the skin to monitor characteristics of the cardiovascular system and communicate such information to another device and/or a caregiver. For example, such a device may monitor pulse rate, oxygenation of the blood, and/or electrical activity of the heart. Similarly, the sensor systems and methods disclosed herein may be utilized for neurophysiological applications, such as monitoring electrical activity of neurons.

The sensor systems and methods disclosed herein may be incorporated into implantable devices, such as implantable orthopedic implants, including flexible implants. Such sensor systems and methods may be configured to collect information regarding the implant site and transmit this information to an external source. In some cases, an internal source may also provide power for such an implant.

The sensor systems and methods disclosed herein may also be utilized for monitoring biochemical activity on the surface of the skin or below the surface of the skin, such as lactose buildup in muscle or sweat production on the surface of the skin. In some cases, other characteristics may be monitored, such as glucose concentration, urine concentration, tissue pressure, skin temperature, skin surface conductivity, skin surface resistivity, skin hydration, skin maceration, and/or skin ripping.

Sensor systems and methods disclosed herein may be incorporated into Ear, Nose, and Throat (ENT) applications. For example, such sensor systems and methods may be utilized to monitor recovery from ENT-related surgery, such as wound monitoring within the sinus passage.

Sensor systems and methods disclosed herein may encompass sensor printing technology with encapsulation, such as encapsulation with a polymer film. Such a film may be constructed using any polymer described herein, such as polyurethane. Encapsulation may provide waterproofing of the electronics and protection from local tissue, local fluids, and other sources of potential damage.

In certain cases, the sensors disclosed herein may be incorporated into an organ protection layer. Such a sensor-embedded organ protection layer may both protect the organ of interest and confirm that the organ protection layer is in position and providing protection. Further, a sensor-embedded organ protection layer may be utilized to monitor the underlying organ, such as by monitoring blood flow, oxygenation, and other suitable markers of organ health. In some cases, a sensor-enabled organ protection layer may be used to monitor a transplanted organ, such as by monitoring the fat and muscle content of the organ. Further, sensor-enabled organ protection layers may be used to monitor an organ during and after transplant, such as during rehabilitation of the organ.

The sensor systems and methods disclosed herein may be incorporated into treatments for wounds (disclosed in greater detail below) or in a variety of other applications. Non-limiting examples of additional applications for the sensor systems and methods disclosed herein include: monitoring and treatment of intact skin, cardiovascular applications such as monitoring blood flow, orthopedic applications such as monitoring limb movement and bone repair, neurophysiological applications such as monitoring electrical impulses, and any other tissue, organ, system, or condition that may benefit from improved sensor-enabled monitoring.

Wound Therapy

Some systems and methods disclosed herein relate to wound therapy for a human or animal body. Therefore, any reference to a wound herein can refer to a wound on a human or animal body, and any reference to a body herein can refer to a human or animal body. The disclosed systems and methods may relate to preventing or minimizing damage to physiological tissue or living tissue, or to the treatment of damaged tissue (for example, a wound as described herein) wound with or without reduced pressure, including for example a source of negative pressure and wound dressing components and apparatuses. The apparatuses and components comprising the wound overlay and packing materials or internal layers, if any, are sometimes collectively referred to herein as dressings. In some cases, the wound dressing can be provided to be utilized without reduced pressure.

As used herein the expression "wound" may include an injury to living tissue may be caused by a cut, blow, or other impact, typically one in which the skin is cut or broken. A wound may be a chronic or acute injury. Acute wounds occur as a result of surgery or trauma. They move through the stages of healing within a predicted timeframe. Chronic wounds typically begin as acute wounds. The acute wound can become a chronic wound when it does not follow the healing stages resulting in a lengthened recovery. It is believed that the transition from acute to chronic wound can be due to a patient being immuno-compromised.

Chronic wounds may include for example: venous ulcers (such as those that occur in the legs), which account for the majority of chronic wounds and mostly affect the elderly, diabetic ulcers (for example, foot or ankle ulcers), peripheral arterial disease, pressure ulcers, pressure injury, or epidermolysis bullosa (EB).

Examples of other wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, pressure injury, stoma, surgical wounds, trauma and venous ulcers or the like.

Wounds may also include a deep tissue injury. Deep tissue injury is a term proposed by the National Pressure Ulcer Advisory Panel (NPUAP) to describe a unique form of pressure ulcers. These ulcers have been described by clinicians for many years with terms such as purple pressure ulcers, ulcers that are likely to deteriorate and bruises on bony prominences.

Wounds may also include a pressure injury. A pressure injury is localized damage to the skin and/or underlying soft tissue, usually over a bony prominence or related to a medical or other device. The injury can present as intact skin or an open ulcer and may be painful. The injury occurs as a result of intense and/or prolonged pressure or pressure in combination with shear. The tolerance of soft tissue for pressure and shear may also be affected by microclimate, nutrition, perfusion, comorbidities and condition of the soft tissue.

Wound may also include tissue at risk of becoming a wound as discussed herein. For example, tissue at risk may include tissue over a bony protuberance (at risk of deep tissue injury/insult) or pre-surgical tissue (for example, knee tissue) that may has the potential to be cut (for example, for joint replacement/surgical alteration/reconstruction).

Some disclosure relates to methods of treating a wound with the technology disclosed herein in conjunction with one or more of the following: advanced footwear, turning a patient, offloading (such as, offloading diabetic foot ulcers), treatment of infection, systemix, antimicrobial, antibiotics, surgery, removal of tissue, affecting blood flow, physiotherapy, exercise, bathing, nutrition, hydration, nerve stimulation, ultrasound, electrostimulation, oxygen therapy, microwave therapy, active agents ozone, antibiotics, antimicrobials, or the like.

Alternatively or additionally, a wound may be treated using topical negative pressure (TNP) and/or traditional advanced wound care, which is not aided by the using of applied negative pressure (may also be referred to as non-negative pressure therapy).

Advanced wound care may include use of an absorbent dressing, an occlusive dressing, use of an antimicrobial and/or debriding agents in a wound dressing or adjunct, a pad (for example, a cushioning or compressive therapy, such as stockings or bandages), or the like.

In some cases, a wound dressing comprises one or more absorbent layer(s). The absorbent layer may be a foam or a superabsorbent.

In some cases, the disclosed technology may be used in conjunction with a non-negative pressure dressing. A non-negative pressure wound dressing suitable for providing protection at a wound site may comprise an absorbent layer for absorbing wound exudate and an obscuring element for at least partially obscuring a view of wound exudate absorbed by the absorbent layer in use. The obscuring element may be partially translucent. The obscuring element may be a masking layer.

In some cases, the non-negative pressure wound dressing as disclosed herein comprises the wound contact layer and the absorbent layer overlies the wound contact layer. The wound contact layer can carry an adhesive portion for forming a substantially fluid tight seal over the wound.

In some cases, the wound dressing as disclosed herein further comprises layer of a superabsorbent fiber, or a viscose fiber or a polyester fiber.

In some cases, the wound dressing as disclosed herein further comprises a backing layer. The backing layer may be a transparent or opaque film. Typically the backing layer comprises a polyurethane film (typically a transparent polyurethane film).

In some cases, the foam may be an open cell foam, or closed cell foam, typically an open cell foam. The foam can be hydrophilic.

The wound dressing may comprise a transmission layer and the layer can be foam. The transmission layer may be a polyurethane foam laminated to a polyurethane film.

The non-negative pressure wound dressing may be a compression bandage. Compression bandages are known for use in the treatment of oedema and other venous and lymphatic disorders, e.g., of the lower limbs. The compression bandage may comprise a bandage system comprising an inner skin facing layer and an elastic outer layer, the inner layer comprising a first ply of foam and a second ply of an absorbent nonwoven web, the inner layer and outer layer being sufficiently elongated so as to be capable of being wound about a patient's limb.

Negative Pressure Wound Therapy

In some cases, treatment of wounds can be performed using negative pressure wound therapy. It will be understood that systems and methods of the present disclosure can be generally applicable for use in TNP systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

Negative pressure therapy can be used for the treatment of open or chronic wounds that are too large to spontaneously close or otherwise fail to heal by means of applying negative pressure to the site of the wound. Topical negative pressure (TNP) therapy or negative pressure wound therapy (NPWT) involves placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. In some cases, the source of negative pressure can be supported by a wound dressing positioned in and/or over the wound. It is believed that such negative pressures promote wound healing by facilitating the formation of granulation tissue at the wound site and assisting the body's normal inflammatory process while simultaneously removing excess fluid, which may contain adverse cytokines or bacteria.

Some of the dressings used in NPWT can include many different types of materials and layers, for example, gauze, pads, foam pads or multi-layer wound dressings. One example of a multi-layer wound dressing is the PICO dressing, available from Smith & Nephew, includes a wound contact layer and a superabsorbent layer beneath a backing layer to provide a canister-less system for treating a wound with NPWT. The wound dressing may be sealed to a suction port providing connection to a length of tubing, which may be used to pump fluid out of the dressing or to transmit negative pressure from a pump to the wound dressing. Additionally, RENASYS-F, RENASYS-G, RENASYS-AB, and RENASYS-F/AB, available from Smith & Nephew, are additional examples of NPWT wound dressings and systems. Another example of a multi-layer wound dressing is the ALLEVYN Life dressing, available from Smith & Nephew, which includes a moist wound environment dressing that is used to treat the wound without the use of negative pressure.

As is used herein, reduced or negative pressure levels, such as $-X$ mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of $-X$ mmHg reflects absolute pressure that is X mmHg below 760 mmHg or, in other words, an absolute pressure of $(760-X)$ mmHg. In addition, negative pressure that is "less" or "smaller" than X mmHg corresponds to pressure that is closer to atmospheric pressure (such as, $-40$ mmHg is less than $-60$ mmHg). Negative pressure that is "more" or "greater" than $-X$ mmHg corresponds to pressure that is further from atmospheric pressure (such as, $-80$ mmHg is more than $-60$ mmHg). In some cases, local ambient atmospheric pressure is used as a reference point, and such local atmospheric pressure may not necessarily be, for example, 760 mmHg.

In some wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via some of the wound closure devices. In some cases, negative pressure may be varied over time for example using a sinusoidal wave, square wave, or in synchronization with one or more physiological indices (such as, heartbeat).

Any of the systems and methods disclosed herein can be used in combination with any of the features disclosed in one or more of WO2010/061225, US2016/114074, US2006/0142560, and U.S. Pat. No. 5,703,225, which describe absorbent materials; WO2013/007973, which describes non-negative pressure wound dressings; GB1618298.2 (filed on 28 Oct. 2016), GB1621057.7 (filed on 12 Dec. 2016), and GB1709987.0 (filed on 22 Jun. 2017), which describe multi-layered wound dressings; EP2498829 and EP1718257, which describe wound dressings; WO2006/110527, U.S. Pat. No. 6,759,566, and US2002/0099318, which describe compression bandages; U.S. Pat. Nos. 8,235,955 and 7,753,894, which describe wound closure devices; WO2013/175306, WO2016/174048, US2015/0190286, US2011/0282309, and US2016/0339158, which describe negative pressure wound therapy dressings, wound dressing components, wound treatment apparatuses, and methods. The disclosure of each of these applications is hereby incorporated by reference in its entirety.

Sensor Enabled Wound Monitoring or Therapy System

FIG. 1A illustrates a wound monitoring or therapy system 10. The system includes a sensor enabled wound dressing 22 connected to a control module 24. As is described herein, the dressing 22 can be placed on or in a wound of a patient and can utilize various sensors embedded or otherwise placed in the dressing 22 to collect measurement data from one or more of the wound or areas surrounding the wound, such as the periwound (which can include intact skin). The control module 24 can receive, store, and process data collected by the dressing 22. To facilitate communication, the dressing 22 can include one or more communication modules, such as one or more antennas as described herein. In some cases, the control module 24 can transmit one or more of commands and data to the dressing 22.

Wound dressing 22 can be disposable and control module 24 can be reusable. In some cases, wound dressing 22 can be reusable. In some cases, control module 24 can be a controller. In some cases, wound dressing 22 can be re-sterilized or otherwise sanitized or disinfected. In some cases, control module 24 can be disposable. In some cases, wound dressing 22 and control module 24 can be permanently connected and the combined wound dressing and control module be disposable, or reusable or re-sterilized or otherwise sanitized or disinfected. The control module 24 can be positioned on the wound dressing 22. The control module 24 can be spatially separated from the wound dressing 22, such as by a cable or another wired or wireless electrical connection. The control module 24 can include a power source (such as a battery), one or more processors, one or more data storage elements, and a communication device. In some cases, the control module 24 can include one or more sensors, such as a temperature sensor or light (or optical) sensors to gather information on patient or environmental conditions located away from the wound dressing 22. In some cases, the one or more sensors of the control module 24 can include an accelerometer, motion sensor or gyroscope.

The wound dressing 22 can include one or more indicators to communicate information to a user. The indicators can be visual, audible, haptic, or tactile. Communicated information can include measurement data, wound status, or the like.

The control module 24 can communicate data to a communication device 30 as requested, periodically, or the like. Communication can be performed over a wired or wireless interface, such as via near field communication (NFC), RFID, or the like when the communication device is placed in communication range. For example, communication range can be close proximity, such as within approximately 3 cm or less or more, to the control module 24. Communication device 30 can be placed in communication range by a clinician, such as during initialization and at the end of treatment. The control module 24 can respond with data to a command from the communication device 30 requesting data. Communication can be performed via transfer of hardware or data storage, such as one or more memory storage devices (for example, SD card). In some cases, communication can be performed non-electronically, such as visually, audibly, or tactilely, and one or more of the control module 24 or communication device 30 can provide an interface for such non-electronic communication of data.

The communication device 30 can be connected via a wired or wireless interface to a computing device 40, such as a personal computer, tablet, smartphone, or the like. For example, wired USB protocol can be used for communication of data between devices 30 and 40. As another example, communication of data can be performed via transfer of hardware or data storage, such as one or more memory storage devices (for example, SD card). In some cases, communication of data can be performed non-electronically, such as visually, audibly, or tactilely, and one or more of the communication device 30 or computing device 40 can provide an interface for such non-electronic communication of data.

Computing device 40 can further process data collected by the dressing 22. For example, the computing device 40 can aggregate data collected from the dressing 22 and perfusion determination device 70, which is configured to determine skin perfusion pressure and communicate data to the computing device 40 via a wired or wireless interface. For example, wired USB protocol can be used for communication between devices 70 and 40.

Computing device 40 can be configured to communicate via a wired or wireless interface with a remote computing device 50 that stores and processes medical data. In some cases, remote computing device 50 can be a cloud computing device, which includes one or more of remote storage, server, processing device, or any means of information storage. For example, remote computing device 50 can process and store medical data according with one or more applicable security and privacy standards, such as Health Insurance Portability & Accountability Act (HIPAA), European Union's Directive on Data Protection, or the like. Remote computing device 50 can make data provided by one or more of the computing device 40 or the mobile device 60 available for remote accessing and viewing, such as on a mobile device 60. In certain implementations, additional data can be added for storage on the remote computing device 50. For example, additional data can be added by the mobile device 60 via a dedicated app, web browser interface, or the like. The remote computing device 50 can process the data from one or more of the wound dressing 22, perfusion determination device 70, or the mobile device and assess or determine treatment plan, such as suggest or adjust one or more treatment therapies.

As described herein, mobile device 60 can take one or more images of a patient's wound. Such data can be transmitted via wired or wireless interface to the remote computing device 50. Although a smartphone is illustrated, mobile device 60 can be any suitable computing device that includes imaging functionality, such as a camera. Mobile device 60 can also collect additional data, such as data input by a healthcare provider in response to a questionnaire.
Sensor Enabled Substrates and Wound Dressings A wound dressing that incorporates a number of electronic components, including one or more sensors, can be utilized in order to monitor characteristics of a wound. Collecting and analyzing data from a wound can provide useful insights towards determining whether a wound is on a healing trajectory, selecting proper therapy, determining whether the wound has healed, or the like.

Figure 1B:
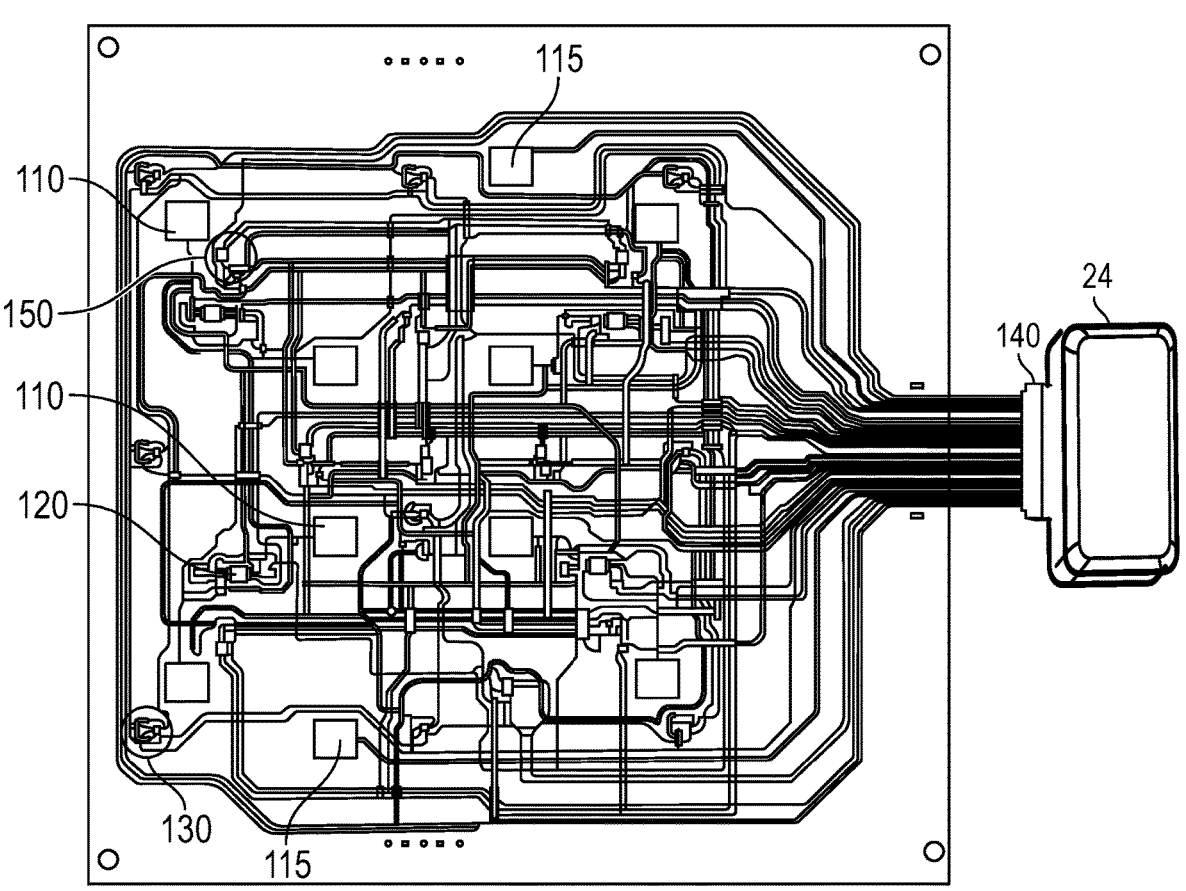
FIGS. 1B-1C illustrate substrates supporting electronic components.
Figure 1C:
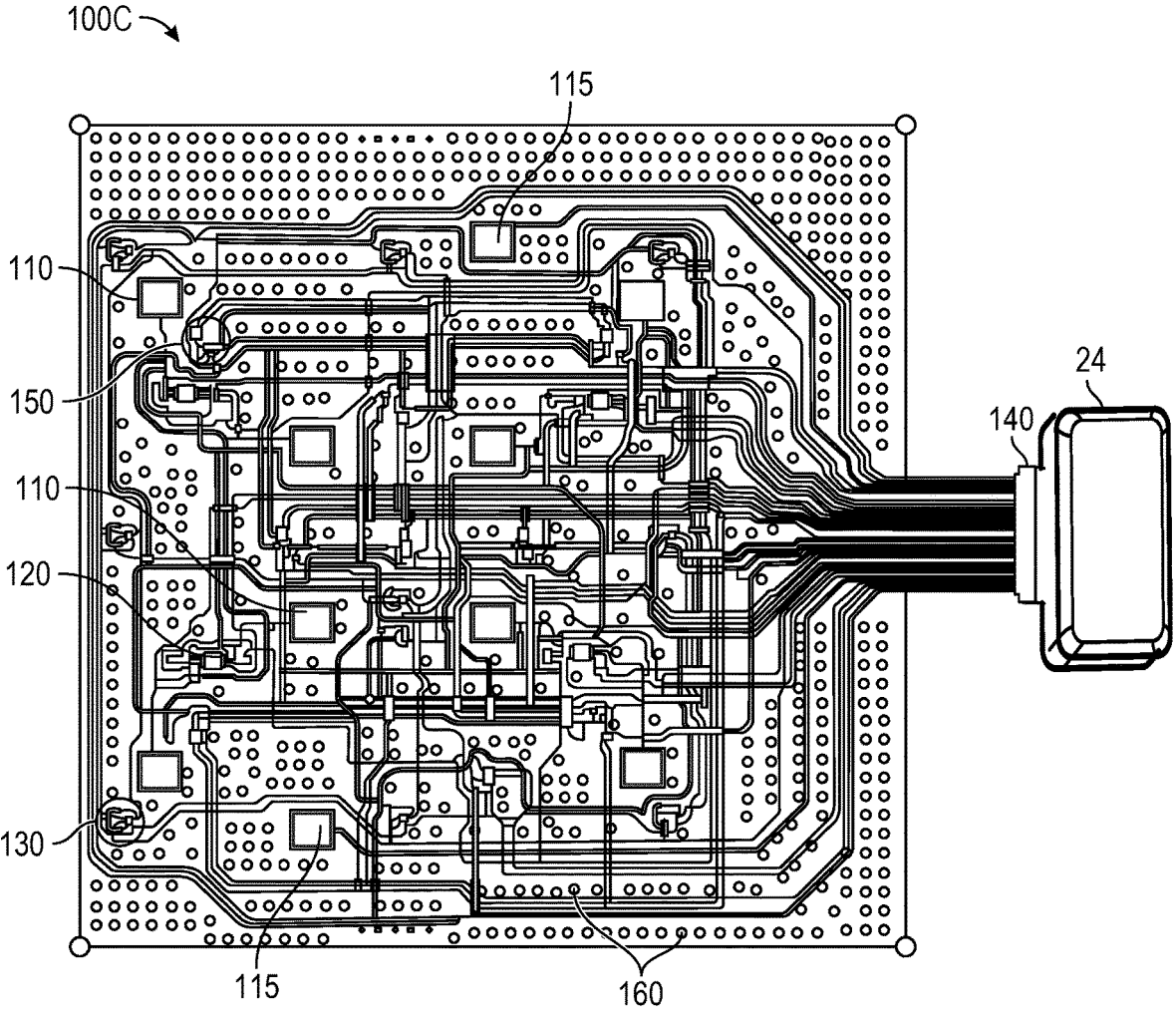

In some implementations, a number of sensor technologies can be used in wound dressings or one or more components forming part of an overall wound dressing apparatus. For example, as illustrated in FIGS. 1B-1C, one or more sensors can be incorporated onto or into a substrate (such substrate can be referred to as "sensor integrated substrate" or "sensor enable substrate"). The substrate is illustrated as having a square shape, but it will be appreciated that the substrate may have other shapes such as rectangular, circular, oval, etc. In some cases, a substrate supporting one or more sensors can be provided as an individual material layer that is placed directly or indirectly over or in a wound. The sensor integrated substrate can be part of a larger wound dressing apparatus. In some cases, the sensor integrated substrate is part of a single unit dressing. Additionally or alternatively, the sensor integrated substrate can be placed directly or indirectly over or in the wound and then covered by a secondary wound dressing, which can include one or more of gauze, foam or other wound packing material, a superabsorbent layer, a drape, a fully integrated dressing like the Pico or Allevyn Life dressing manufactured by Smith & Nephew, or the like.

The sensor integrated substrate can be placed in contact with a wound and can allow fluid to pass through the substrate while causing little to no damage to the tissue in the wound. The substrate can be flexible, elastic, extensible, or stretchable or substantially flexible, elastic, extensible, or stretchable in order to conform to or cover the wound. For example, the substrate can be made from a stretchable or substantially stretchable material, such as one or more of polyurethane, thermoplastic polyurethane (TPU), silicone, polycarbonate, polyethylene, polyimide, polyamide, polyester, polyethelene tetraphthalate (PET), polybutalene tetreaphthalate (PBT), polyethylene naphthalate (PEN), polyetherimide (PEI), along with various fluropolymers (FEP) and copolymers, or another suitable material.

Stretchable or substantially stretchable material can be stretched to 5% or less or more, 10% or less or more, 20% or less or more, or more than 20% of its starting dimensions, such as length or width. In some cases, the stretchable or substantially stretchable material can return to within 5% or less or more of the starting dimensions (such as length or width) after being stretched.

In some cases, the substrate can include one or more flexible circuit boards, which can be formed of flexible polymers, including polyamide, polyimide (PI), polyester, polyethylene naphthalate (PEN), polyetherimide (PEI), along with various fluropolymers (FEP) and copolymers, or the like. One or more sensors can be incorporated into a two-layer flexible circuit board. In some scenarios, the one or more circuit boards can be a multi-layer flexible circuit board.

In some cases, the sensor integrated substrate can incorporate adhesive, such as a wound contact layer as described herein, that adheres to wet or dry tissue. In some cases, one or more sensors, which can be positioned one or more flexible circuits boards, can be incorporated into any layer of the wound dressing. For example, a wound contact layer can have cutouts or slits that allow for one or more sensors to protrude out of the lower surface of the wound contact layer and contact the wound directly. In some situations, one or more sensors can be incorporated into or encapsulated within other components of a wound dressing, such as an absorbent layer.

As shown in FIG. 1B, a sensor integrated substrate 100B can support a plurality of electronic components and a plurality of electronic connections interconnecting at least some of the components. The electronic components can be one or more of any electronic components described herein, such as a sensor, amplifier, capacitor, resistor, inductor, controller, processor, diode, or the like. The electronic connections can electrically connect one or more of the electronic components. The electronic connections can be can be traces or tracks printed on the substrate, such as using copper, conductive ink (such as silver ink, graphite ink, carbon ink, etc.), or the like. At least some of the electronic connections can be flexible or stretchable or substantially flexible or stretchable.

The plurality of electronic components can include one or more impedance or conductivity sensors 110, which can be arranged in an outer 4×4 grid and an inner 4×4 grid as illustrated in FIGS. 1B-1C. Sensors 110 are illustrated as pads configured to measure impedance or conductivity of tissue across any pair of the pads. Two (or more) excitation pads 115 can be arranged as illustrated to provide the excitation signal across the pads, which is conducted by the tissue and responsive to which impedance or conductance of the tissue can be measured across the pads 110. Electronic components, such as one or more amplifiers 120, can be used to measure impedance or conductance of the tissue. Impedance or conductance measurements can be used to identify living and dead tissue, monitor progress of healing, or the like. The arrangement of the pads 110 in the inner and outer grids can be used to measure the impedance or conductance of the wound, perimeter of the wound, or tissue or areas surrounding the wound.

The plurality of electronic components can include one or more temperature sensors 130 configured to measure temperature of the wound or surrounding tissue. For example, nine temperature sensors arranged around the perimeter of the substrate 100B. One or more temperature sensors can include one or more thermocouples or thermistors. One or more temperature sensors can be calibrated and the data obtained from the one or more sensors can be processed to provide information about the wound environment. In some cases, an ambient sensor measuring ambient air temperature can also be used to assist in eliminating problems associated with environment temperature shifts.

The plurality of electronic components can include one or more optical sensors 150. One or more optical sensors 150 can be configured to measure wound appearance or image the wound. In some cases, a light source or illumination source that emits light and a light sensor or detector that detects light reflected by the wound are used as one or more optical sensors. The light source can be a light emitting diode (LED), such as one or more of white LED, red, green, blue (RGB) LED, ultraviolet (UV) LED, or the like. The light sensor can be one or more of an RGB sensor configured to detect color, infrared (IR) color sensor, UV sensor, or the like. In some cases, both the light source and detector would be pressed up against the skin, such that light would penetrate into the tissue and take on the spectral features of the tissue itself. In some scenarios, one or more optical sensor can include an imaging device, such as a charge-coupled device (CCD), CMOS image sensor, or the like.

In some cases, ultra-bright LEDs, an RGB sensor, and polyester optical filters can be used as components of the one or more optical sensors to measure through tissue color differentiation. For example, because surface color can be measured from reflected light, a color can be measured from light which has passed through the tissue first for a given geometry. This can include color sensing from diffuse scattered light, from an LED in contact with the skin, or the like. In some cases, an LED can be used with a proximal RGB sensor to detect the light which has diffused through the tissue. The optical sensors can image with diffuse internal light or surface reflected light.

One or more of the plurality of electronic components can be controlled by a control module. The control module can receive and process one or more measurements obtained by the one or more sensors. An external control module, such as 24 illustrated in FIG. 1A, can be connected to at least some of the plurality of electronic components via a connector (for example, connector 140 in FIGS. 1B-1C). In some cases, the connector 140 can be positioned at the end of a conductive track portion as illustrated in FIG. 1C or attached to the conductive track portion at a position away from the end as illustrated in FIG. 1B (such as, attached to the top of the track portion with glue). The control module can include one or more controllers or microprocessors, memory, or the like. In some cases, one or more controllers can be positioned on the substrate, and the connector 140 is not used. In some cases, data and commands can be communicated wirelessly, such as by a transceiver positioned on the substrate, and the connector 140 is not used.

In some cases, additional or alternative sensors can be positioned on the substrate, such as one or more pH sensors, pressure sensors, perfusion sensors, or the like.

In some cases, a substrate can be perforated as illustrated in FIG. 1C. A plurality of perforations 160 can be formed in the substrate 100C, allowing fluid to pass through the substrate. It may be advantageous to use a perforated substrate in conjunction with application of negative pressure wound therapy, during which reduced pressure is applied to the wound covered by a dressing and which causes removal of fluid (such as wound exudate) from the wound. Perforations 160 can be formed around a plurality of electronic components and connections as illustrated in FIGS. 1B-1C.

Perforations 160 can be formed as slits or holes. In some cases, perforations 160 can be small enough to help prevent tissue ingrowth while allowing fluid to pass through the substrate.

In some cases, the substrate can be coated to encapsulate or coat one or more of the substrate or components supported by the substrate. Coating can provide biocompatibility, shield or protect the electronics from coming into contact with fluids, provide padding for the electronic components to increase patient comfort, or the like. Such coating can be sometimes referred to as "conformal coat" or "soft coat." Soft coat can be stretchable or substantially stretchable. Soft coat can be hydrophobic or substantially hydrophobic.

Soft coat can be formed from one or more suitable polymers, adhesives, such as 1072-M adhesive (for example, Dymax 1072-M), 1165-M adhesive (such as, Dymax 1165-M), parylene (such as, Parylene C), silicones, epoxies, urethanes, acrylated urethanes, acrylated urethane alternatives (such as, Henkel Loctite 3381), or other suitable biocompatible and substantially stretchable materials. Soft coat can be thin coating, for example, from about 80 microns or less up to several millimeters or more. Soft coat can have hardness lower than about A100, A80, A50 or lower. Soft coat can have elongation at break higher than about 100%, 200%, 300% or more. Soft coat can have viscosity of about 8,000-14,500 centipoise (cP). In some cases, coating can have viscosity no less than about 3,000 cP. In some cases, coating can have viscosity less than about 3,000 cP.

In some cases, while it may be desirable for a substrate to be stretchable or substantially stretchable to better conform to or cover the wound, at least some of the electronic components or connections may not be stretchable or flexible. In such instances, undesirable or excessive localized strain or stress may be exerted on the one or more electronic components, such as on the supporting area or mountings of an electronic component, when the substrate is positioned in or over the wound. For example, such stress can be due to patient movement, changes in the shape or size of the wound (such as, due to its healing), or the like. Such stress may cause movement, dislodgment, or malfunction of the one or more electronic components or connections (for example, creation of an open circuit from a pin or another connector becoming disconnected). Alternatively or additionally, it may be desirable to maintain the position of one or more electronic components, such as one or more sensors, in the same or substantially same location or region with respect to the wound (such as, in contact with the wound) so that measurements collected by the one or more electronic components accurately capture changes over time in the same or substantially same location or region of the wound. While the surface of the stretchable substrate may move when, for example, the patient moves, it may be desirable to maintain same or substantially same locations of one or more electronic components relative to the wound.

To address these problems, in some cases, non-stretchable or substantially non-stretchable coating (such coating can sometimes be referred to as "hard coat") can be applied to one or more electronic components, one or more electronic connections, or the like. Hard coat can provide one or more of reinforcement or stress relief for one or more electronic components, one or more electronic connections, or the like. Hard coating can be formed from acrylated or modified urethane material. For example, hard coat can be one or more of Dymax 1901-M, Dymax 9001-E, Dymax 20351, Dymax 20558, Henkel Loctite 3211, or another suitable material. Hard coat can have viscosity from about 13,500 cP to 50,000 cP before being cured or from about 3,600 cP to about 6,600 cP before being cured. In some cases, hard coat can have viscosity of no more than about 50,000 cP. Hard coat can have hardness from about D40 to about D65 and/or linear shrinkage of about 1.5-2.5%.

Any of the hard or soft coats described herein can be applied by one or more of laminating, adhering, welding (for instance, ultrasonic welding), curing by one or more of light, UV, thermal (such as, heat), or the like. Any of the hard or soft coat described herein can be transparent or substantially transparent to facilitate transmission of light through the coating, such as for optical sensing. Any of the coatings described herein can retain bond strength when subjected to sterilization, such as EtO sterilization. Any of the coatings described herein can be modified to fluoresce, such as under UV light.

In some implementations, borders or edges of the substrate can be smoothed by cuts, have smooth contours, include fibers, or the like to improve patient comfort.

In some cases, the substrate can include one or more antennas for wireless communication. For example, one or more antennas can be printed as one or more connections or traces on the substrate. The one or more antennas can be used to communicate measurement data collected by the one or more sensors without using a controller, such as the control module 24. The one or more antennas can additionally be used to receive power wirelessly from a power source. In certain cases, the one or more antenna traces can be positioned on a substantially non-stretchable material (as described herein) such that the resonant frequencies of the one or more antennas remain fixed when the substrate is placed under stress when in use on a patient. Fixing the one or more resonant frequencies can be advantageous for certain communication protocols, such as RFID.

Sensor Substrate Connector

In some cases, an integrated or external control module, such as the control module 24 illustrated in any of FIGS. 1A-1C, can be connected to at least some of the plurality of electronic components via the connector 140. The electronic connections between the electronic components and the connector 140 or the connector 140 and the control module can be traces or tracks printed on the substrate, such as using copper, conductive ink (such as silver ink, graphite ink, carbon ink, etc.), cables, wires, or the like. At least some of the electronic connections can be flexible or stretchable or substantially flexible or stretchable. For example, in some cases, the electronic connections can include silver ink printed on a substrate, which can be formed from Thermoplastic Polyurethane (TPU) (for example, 40 um thick).

Figure 2:
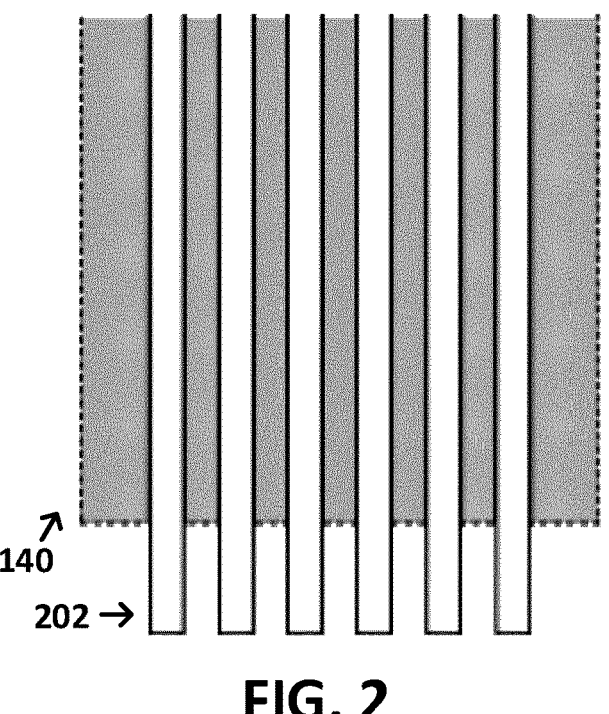
FIG. 2 illustrates a connector.

FIG. 2 illustrates the connector 140. In some cases, the connector 140 can be made more rugged such that the electrical connections are less vulnerable to malfunction or damage during flexion. For example, in some cases, the connector 140 is designed to reduce flexion of the electrical connections. The connector 140 can provide structure or support that limits movement or flexion of the electrical connections.

The connector 140 can be positioned at an end of the substrate so as to provide a stronger contact to a control module connector. In some cases, at least a portion of the connector 140 can be bonded or otherwise attached to at least a portion of the substrate or at least a portion of a wound dressing, such as wound dressing 22 of FIG. 1A. For example, the connector 140 can include flexible substrates, such as polyimide, polyether ether ketone (PEEK), or transparent conductive polyester film. In some cases, the connector 140 can be at least partially bonded to the substrate using the same methods used for bonding at least some of the plurality of electronic components to the substrate. As illustrated, in some cases, the connector 140 can include a plurality of exposed leads 202 for connecting to the electrical connections of the electronic components or the control module.

Dressing-to-Controller Connections

Figure 3:
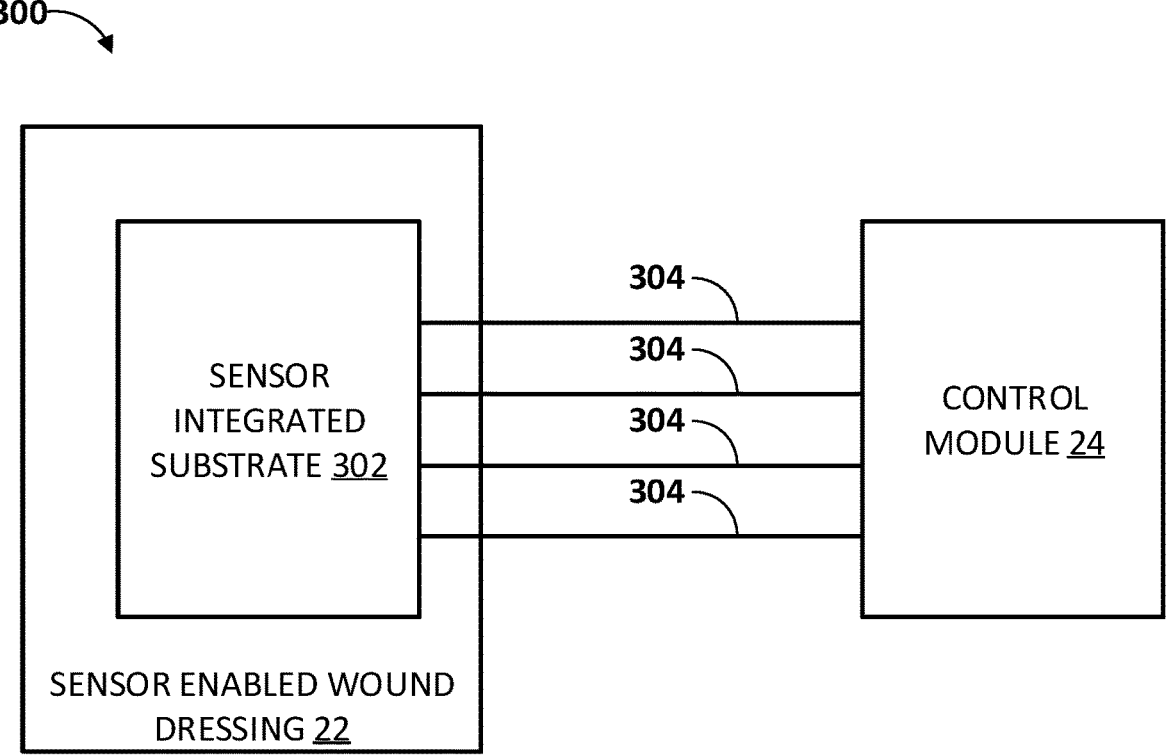
FIG. 3 illustrates a wound monitoring or therapy system.

FIG. 3 illustrates a wound monitoring or therapy system 300. The wound monitoring or therapy system 300 can include a control module 24 and a sensor enabled wound dressing 22 that can include a sensor integrated substrate 302. The sensor integrated substrate 302 can be similar to one or both of the sensor integrated substrates 100B or 100C FIG. 1B or 1C. The sensor integrated substrate 302 or the control module 24 can include a plurality of electronic components and a plurality of electronic connections interconnecting at least some of the electronic components.

The electronic components can be one or more of any electronic components described herein, such as a sensor, amplifier, capacitor, resistor, inductor, controller, processor, diode, digital-to-analog converter (DAC), analog-to-digital converter (ADC), or the like. The sensor enabled wound dressing 22 can be placed on or in a wound of a patient and can utilize the various electronic components to collect measurement data from one or more of the wound or areas surrounding the wound, such as the periwound (which can include intact skin).

A plurality of electronic connections can interconnect at least some of the electronic components of the sensor enabled wound dressing 22 or the control module 24. At least some of these electronic connections can be traces or tracks printed on the sensor integrated substrate 302, such as using copper, conductive ink (such as silver ink, graphite ink, carbon ink, etc.), wires, cables, or other physical electrical connections. At least some of these electronic connections can extend between the sensor enabled wound dressing 22 and the control module 304. The electronic connections that extend between the sensor enabled wound dressing 22 and the control module 304 can be individually or collectively referred to as dressing-to-controller connections 304.

Although only four dressing-to-controller connections 304 are illustrated in FIG. 3, the present disclosure is not to be construed as being so limited, as the wound monitoring or therapy system 300 may include a fewer or greater number of dressing-to-controller connections 304. For example, the wound monitoring or therapy system 300 may include a single or a few dressing-to-controller connections 304, or can include about 5, 10, 20, 25, 40, or more dressing-to-controller connections 304.

In some cases, dressing-to-controller connections 304 can be damaged as a result of flexion or other forces applied to the components of the system 300. Such forces can result from movement of a user wearing the dressing 22 or the control module 24. Large number of dressing-to-controller connections 304 can result in high density of connections on a substrate connecting the dressing 22 to the control module 24 as shown in FIGS. 1B and 1C. This can lead to signal degradation due to cross-talk, parasitic capacitance, or the like. Accordingly, it may be desirable to reduce the number of dressing-to-controller connections 304 or eliminate them altogether.

The number of dressing-to-controller connections 304 can depend, for example, on the number of the electronic components and position or location of the electronic components within the wound monitoring or therapy system 300. For example, as described herein, the sensor enabled wound dressing 22 can include a number of sensors mounted on or embedded within the sensor integrated substrate 302.

In some cases, each individual sensor can be in electrical communication with the control module 24 via a different physical connection 304. In some cases, some or all of the sensors can be in electrical communication with the control module 24 via one or more dressing-to-controller connections 304.

In some cases, the number of dressing-to-controller connections 304 can be based at least in part on the locations, within the wound monitoring or therapy system 300, of electronic components. For example, in some implementations, the wound monitoring or therapy system 300 includes fewer dressing-to-controller connections 304 when the sensor enabled wound dressing 22, as opposed to the control module 24, includes certain electronic components. By incorporating additional electronic components into the sensor enabled wound dressing 22, and thus removing these electronic components from the control module 24, the number of dressing-to-controller connections 304 can be reduced. For example, when electronic components are moved to the sensor enabled wound dressing 22 (for example, onto the sensor integrated substrate 302), at least some of the electrical connections between those electronic components can be implemented as traces, track, or other connections on the sensor integrated substrate 302, rather than dressing-to-controller connections 304.

In some cases, some or all of the receiving, storing, and processing of data collected by the sensor enabled wound dressing 22 is performed on the sensor enabled wound dressing 22, such as by a control module (for example, control module 24 of FIG. 4A) attached to or integrated with the sensor enabled wound dressing 22 or the sensor integrated substrate 302. For example, in some cases, the control module 24 may only provide power and ground connections to the sensor enabled wound dressing 22. In this way, the control module 24 can be simplified, yet can retain the power source for the sensor integrated substrate 302, which can mitigate any health risks of integrating the power source into the sensor integrated substrate 302. Data collected by one or more sensors of the wound dressing 22 can be transmitted wirelessly, such as via electromagnetic waves transmitted by one or more antennas of the wound dressing 22, optically, or the like. In such cases, the number of dressing-to-controller connections 304 can be reduced to two. In some cases, power or ground connections can be eliminated by adding a battery or another source of power to the sensor enabled wound dressing 22 or the sensor integrated substrate 302. In such cases, all dressing-to-controller connections 304 can be eliminated.

In some cases, a plurality of perforations can be formed in a sensor integrated substrate 302 as depicted in FIG. 1C. The positioning of perforations, such as one or more of the size, number, density, or distance between adjacent perforations, can be dictated by a particular monitoring or therapy application in which the sensor integrated substrate 302 will be used, such as negative pressure wound therapy. For example, it may be desirable to form perforations of a particular minimum size and at a particular maximum distance from adjacent one or more perforations in order to ensure that fluid moves through the sensor integrated substrate 302 without undesirable pooling at a region of the wound below the sensor integrated substrate 302 (which can cause maceration of skin, infection, or the like). On the other hand, because it may be undesirable to form perforations through the electronic components and connections, positioning of the perforations can provide a set of limitations or constraints on the dimensions and positioning on the substrate of the electronic components and connections to ensure that the electronics positioned on the substrate functions correctly and efficiently.

Perforations can be formed as slits or holes. In some cases, perforations can be small enough to help prevent tissue ingrowth while allowing fluid to pass through the substrate. Exudate can be removed through perforations, which can limit or prevent exudate pooling. In some cases, the shape of the dressing 22 permits for efficient removal of wound exudate and reduction or prevention of pooling. In some cases, to further improve exudate management, one or more perforations can be made to permit flow of exudate.

In some cases, it may be desirable to keep the electronic components or connections isolated from fluid. It may be advantageous to include one or more openings or perforations in a substrate of any of the wound dressings or sensor arrays disclosed herein to allow wound exudate to be removed. Managing wound exudate to limit or prevent pooling of exudate in the wound can facilitate more effective healing of the wound. For example, perforations can be made around the perimeter of the substrate. The one or more perforations can be made around the traces connecting the sensors. The one or more perforations can be formed as any suitable shape or pattern. For example, the one or more perforations can be shaped as triangles, rectangles, squares, circles, ovals, or the like.

Local Controller

Figure 4A:
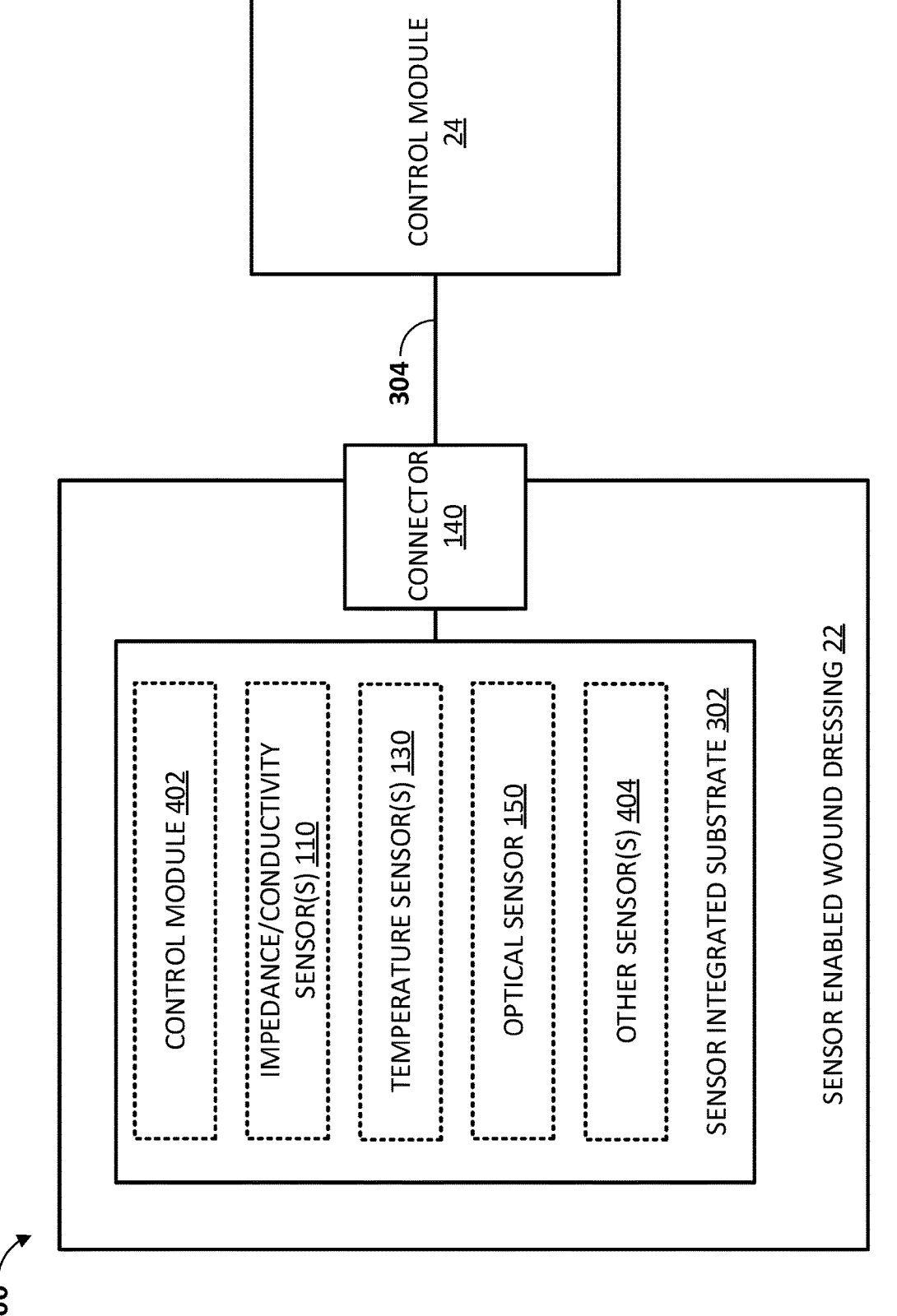
FIG. 4A illustrates a wound monitoring or therapy system.

FIG. 4A illustrates a wound monitoring or therapy system 400. The wound monitoring or therapy system 400 can be similar to the wound monitoring or therapy system 300 of FIG. 3. For example, similar to the wound monitoring or therapy system 300, the wound monitoring or therapy system 400 can include a sensor enabled wound dressing 22 and a control module 24, and the sensor enabled wound dressing 22 can include a sensor integrated substrate 302. In addition, in this example, the sensor enabled wound dressing 22 can include a control module 402, such as a controller, processor, or the like.

As described herein, the wound monitoring or therapy system 400 can include a plurality of electronic components in the sensor enabled wound dressing 22, the sensor integrated substrate 302, or the control module 24. For instance, in the illustrated example, the sensor integrated substrate 302 can include one or more of: one or more impedance or conductivity sensors 110, one or more temperature sensors 130, one or more optical sensors 150, or one or more other sensors 404. In some cases, additional or alternative sensors can be positioned on the sensor integrated substrate 302, such as one or more pH sensors, pressure sensors, perfusion sensors, or the like.

The control module 24 can be external to the wound dressing 22. As illustrated, the control module 24 can be connected to the sensor enabled wound dressing 22, or components thereon, via one or more of dressing-to-controller connections 304, which can be part of the connector 140.

In some implementations, the control module 24 is internal to the wound dressing 22. For example, the control module 24 can be attached to or integrated with the wound dressing 22, such as supported by the substrate 302. In some cases, the control module 24 can be connected to at least some of the plurality of electronic components via a plurality of electronic connections. For example, the electronic connections connecting the control module 24 can be similar to the electronic connections that interconnect at least some of the electronic components, as described herein.

One or both of the control modules 24 or 402 can include one or more controllers or microprocessors, memory, or the like. Some or all of the plurality of electronic components can be controlled or operated by either or both of control module 24 or control module 24. Furthermore, either or both of control module 24 or control module 24 can receive or process one or more measurements obtained by the one or more sensors 110, 130, 150, or 404.

In some cases, the control modules 24 and 402 can work together to receive, store, and process data collected by the one or more sensors of the sensor enabled wound dressing 22. For example, the control modules 24 and 402 can work as co-processors. As another example, one of the control modules 24 or 402 can act as a primary processor, while the other acts as a secondary processor. For example, in some cases, the control module 24 can be configured for dedicated tasks, such as for processing one or more of temperature, optical (or light), impedance, or capacitive sensing. In some cases, the control module 24 can perform at least some of the collection and processing of the data, and can provide the at least some of the collected or processed data to the control module 24, for example to store, communicate to an external computing device, or process further. As another example, in some cases, the control module 24 can perform at least some of the collection and processing of the data, and the control module 24 can provide the at least some of the collected or processed data to the control module 24, for example to store, communicate to an external computing device, or process further.

The control module 24 and control module 24 can be configured to communicate uni-directionally or bi-directionally (for example via a serial bidirectional communication protocol, such as Local Interconnect Network (LIN)). For example, uni-directional or bi-directional communication can be established optically. In some cases, the one or more coatings described herein can act as a light guide facilitating transmission of light. As described herein, coating can be optically transparent or substantially optically transparent. The optical communication can be performed at the edge or corner of the substrate 302, which can be advantageous for placing one or more light emitters or sources (such as, LEDs) or one or more light detectors away from the other components positioned on the substrate 302 or away from one or more areas with perforations or in an area of the substrate in which density or number of perforations is less than a threshold. In some cases, the density or number of perforations does not substantially affect the optical communications. In some cases, optical communication can be performed using infrared (IR) communication, such as using one or more of Infrared Data Association (IrDA) protocols, Consumer IR (CIR) protocols, or the like. In some cases, each of the control module and the substrate can include light emitters and detectors for optical communication. In some cases, the communication can be via a serial protocol, such as via the Inter-integrated Circuit (I2C) Protocol. In some cases, optical communication can be improved by using components that are reverse-mounted (for example, inserted through a hole of the substrate 302 and coated). For example, the optical communication can be performed by one or more reverse mounted LEDs or IR components. In this way, the coating over the substrate can create a flexible light communication path to the control module 24.

The control module 24 can be in electrical communication with a plurality of sensors of the sensor enabled wound dressing 22 or of the sensor integrated substrate 302. The sensors can include, but are not limited to, one or more temperature sensors, optical sensors, impedance sensors, conductivity sensors, accelerometers, motion sensors, gyroscopes, pH sensors, pressure sensors, or perfusion sensors.

In some cases, the plurality of sensors includes multiple sensors of the same type, such as multiple temperature sensors, multiple impedance sensors, or multiple optical sensors. In some cases, the plurality of sensors include multiple sensors of different types, such as at least one temperature sensor, at least one optical sensor, and at least one impedance sensor as described herein.

The control module 24 can receive sensor data, for example in the form of one or more signals, from one or more of the plurality of sensors. The signals can correspond to measurements taken by the sensors. For example, the control module 24 can communicate with at least some of the plurality of sensors to activate at least one first sensor and at least one second sensor. In some cases, prior to activation of the at least one first and second sensors, the control module 24 can receive one or more control commands from the control module 24. In some cases, the control module 24 can activate the at least one first and second sensors based at least in part on the control commands.

The control module 24 can receive sensor data from a plurality of sensors. In some cases, at least some of the sensor data is digital data. For example, one or more of the plurality of sensors (for example, one or more optical sensors) can produce digital sensor data and provide it to the control module 24. In some cases, at least some of the sensor data is analog sensor data. For example, one or more of the plurality of sensors (for example, one or more temperature sensors) can produce analog sensor data, which can pass through an analog-to-digital converter (ADC) prior to as part of being received by the control module 24. As another example, one or more of the plurality of sensors (for example, an optical sensor) can produce digital sensor data, which can pass through a digital-to-analog converter (DAC) prior to or as part of being received by the control module 24

In some cases, the control module 24 can store the sensor data in a memory or process the sensor data. In addition to or alternatively, the control module 24 can communicate at least some of the received sensor data to the control module 24. In some cases, the control module 24 can provide digital sensor data to the control module 24. For example, the control module 24 can digitize (for example, using an ADC) some of all analog sensor data before communicating it to the control module 24. In some cases, the control module 24 can provide analog sensor data to the control module 24. For example, the control module 24 can convert some or all of the sensor data to analog sensor data (for example, using a DAC) before communicating it to the control module 24.

Figure 4B:
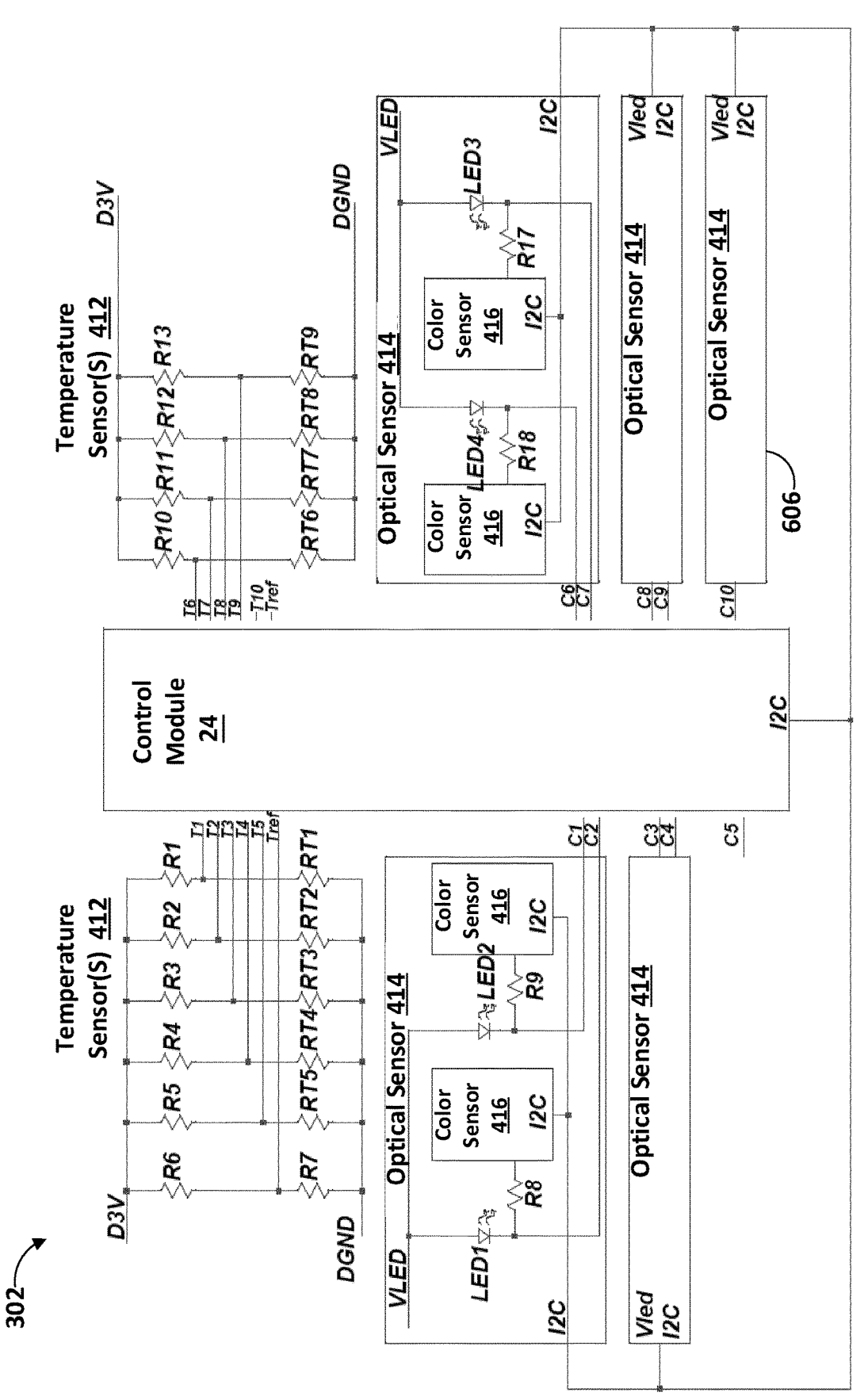
FIG. 4B illustrates an example sensor integrated substrate.

FIG. 4B illustrates an example sensor integrated substrate 302. As illustrated, the sensor integrated substrate 302 includes a control module 24, a plurality of temperature sensors 412, and a plurality of optical sensors 414. For simplicity, the temperature sensors 412 can be described generally as temperature sensor 412. However, one or more of the temperature sensors 412 may be configured differently, and it should be understood that any description of a temperature sensor 412 may apply to one or more of the temperature sensors 412 and may or may not apply to each of the temperature sensors 412. Furthermore, for simplicity, the optical sensors 414 can be described generally as optical sensor 414. However, one or more of the optical sensors 414 may be configured differently, and it should be understood that any description of an optical sensors 414 may apply to one or more of the optical sensors 414 and may or may not apply to each of the optical sensors 414.

As is illustrated, the plurality of temperature sensors 412 includes nine temperature sensors. However, fewer or additional temperature sensors 412 can be used. Each temperature sensor 412 can include a thermistor in series with a resister Each of the nine temperature sensors 412 can include a series thermistor-resistor combination, in the form of a voltage divider. For example, a first temperature sensor can include resistor R1 connected to a reference voltage (labeled D3V) and in series with a thermistor RT1 connected to ground (labeled DGND), a second temperature sensor can include resistor R2 connected to the reference voltage and in series with a thermistor RT2 connected to ground, a third temperature sensor can include resistor R3 connected to the reference voltage and in series with a thermistor RT3 connected to ground, a fourth temperature sensor can include resistor R4 connected to the reference voltage and in series with a thermistor RT4 connected to ground, a fifth temperature sensor can include resistor R5 connected to the reference voltage and in series with a thermistor RT5 connected to ground, a sixth temperature sensor can include resistor R10 connected to the reference voltage and in series with a thermistor RT6 connected to ground, a seventh temperature sensor can include resistor R11 connected to the reference voltage and in series with a thermistor RT7 connected to ground, an eighth temperature sensor can include resistor R12 connected to the reference voltage and in series with a thermistor RT8 connected to ground, and a ninth temperature sensor can include resistor R13 connected to the reference voltage and in series with a thermistor RT9 connected to ground.

In the illustrated example, the output voltage of the voltage divider of each temperature sensor 412 is connected to a respective analog signal input (labeled T1 to T9) of the control module 24. In addition, the sensor integrated substrate 302 can include a circuit (sometimes referred to as circuitry) for generating a reference temperature (labeled Tref), which can include resistor R6 connected to the reference voltage and in series with a resistor R7 connected to ground. Reference temperature circuit can provide reference voltage (or current) corresponding to a known temperature values, such as 37 degrees Celsius or another suitable temperature. Such reference voltage (or current) can be used to determine temperature values of the temperature sensors 412. It will be understood that the sensor integrated substrate 302 can include fewer or additional temperature sensors 412. Furthermore, any of the temperature sensors 412 can be arranged differently, such as by switching the location of a resistor and a thermistor.

The optical sensors 414 can include one or more light emitting diodes (LEDs), resistors, color sensors, or the like. For example, as illustrated, a first optical sensor can include a voltage source VLED, light sources LED1 and LED2, resistors R8 and R9, and color sensors 416. As another example, a second optical sensor can include a voltage source VLED, light sources LED3 and LED4, resistors R18 and R17, and color sensors 416. In the illustrated example, the output of each optical sensor 414 is connected to a respective digital signal input of the control module 24, such as general purpose input/output (GPIO) input.

In some cases, the control module 24 can communicate with one or more of the temperature sensors 412 to activate the one or more the temperature sensors 412. In some cases, the one or more temperature sensors 412 can provide temperature measurements without being activated. The one or more temperature sensors 412 can obtain sensor data corresponding one or more temperature measurements of the wound or periwound, and the sensor data can be provided to the control module 24. As is illustrated, the temperature sensors 412 provide the control module 24 with analog sensor data corresponding to the temperature. However, in some cases, the temperature sensors 412 provide the control module 24 with digital sensor data, or an ADC can be located between a temperature sensor 412 and the control module 412.

In some cases, the control module 24 can communicate with one or more of the optical sensors 414 to activate the one or more the optical sensors 414. In some cases, the one or more optical sensors 414 can provide optical measurements without being activated. The one or more optical sensors 414 can obtain sensor data corresponding one or more optical measurements of the wound or periwound, and the sensor data can be provided to the control module 24. As is illustrated, the optical sensors 414 provide the control module 24 with digital sensor data. For example, each of the sensors 416 can be a digital color-sensor integrated circuit (IC), and each of the color sensors 416 can sense light reflected by the tissue, such as red, green, or blue (RGB) light, and convert the light to digital values. However, in some cases, the optical sensors 414 provide the control module 24 with analog sensor data. For example, the optical sensors 414 can be analog sensors or a DAC can be located between an optical sensor 414 and the control module 412.

In some cases, one or more of the plurality of sensors can communicate with the control module 24 using a serial protocol, such as the I2C protocol. For example, the color sensors 416 can include an I2C bus interface over which data can be communicated to the control module 24. In some cases, multiple control modules 402 can be used.

The control module 24 can communicate with an external computing device, such as the control module 24, using a digital communication protocol. For example, I2C protocol (which requires only clock and data lines) can be used for communication. With the approach illustrated in FIG. 4B, the number of dressing-to-controller connections 304 can be reduced by 15 (9 lines for each of the temperatures sensors and 6 lines for each of the optical sensors), 17 (9 lines for each of the temperatures sensors and 6 lines for each of the optical sensors as well as 2 lines for analog power and ground for the temperature sensors), or the like.

Although the sensor integrated substrate 302 of FIG. 4B illustrates only two types of sensors (temperature and optical), the sensor integrated substrate 302 can include additional or different types of sensors, as desired. For example, the sensor integrated substrate 302 can include one or impedance sensors, conductivity sensors, accelerometers, motion sensors, gyroscopes, pH sensors, pressure sensors, or perfusion sensors.

Merging Signals

In some cases, the number of dressing-to-controller connections 304 can be additionally or alternatively reduced by combining one or more signals to reduce an overall number of signals being transmitted to the control module 24. For example, in some cases, signals at different frequencies can be combined and transmitted to the control module 24 in a single signal. The control module 24 can receive the combined signal and can decompose the received combined signal into the original sensor signals. In some cases, this technique can be applied without introducing distortion into any of the original sensor signals. In some cases, this technique can be applied while introducing little or any distortion into the original sensor signals.

Figure 5A:
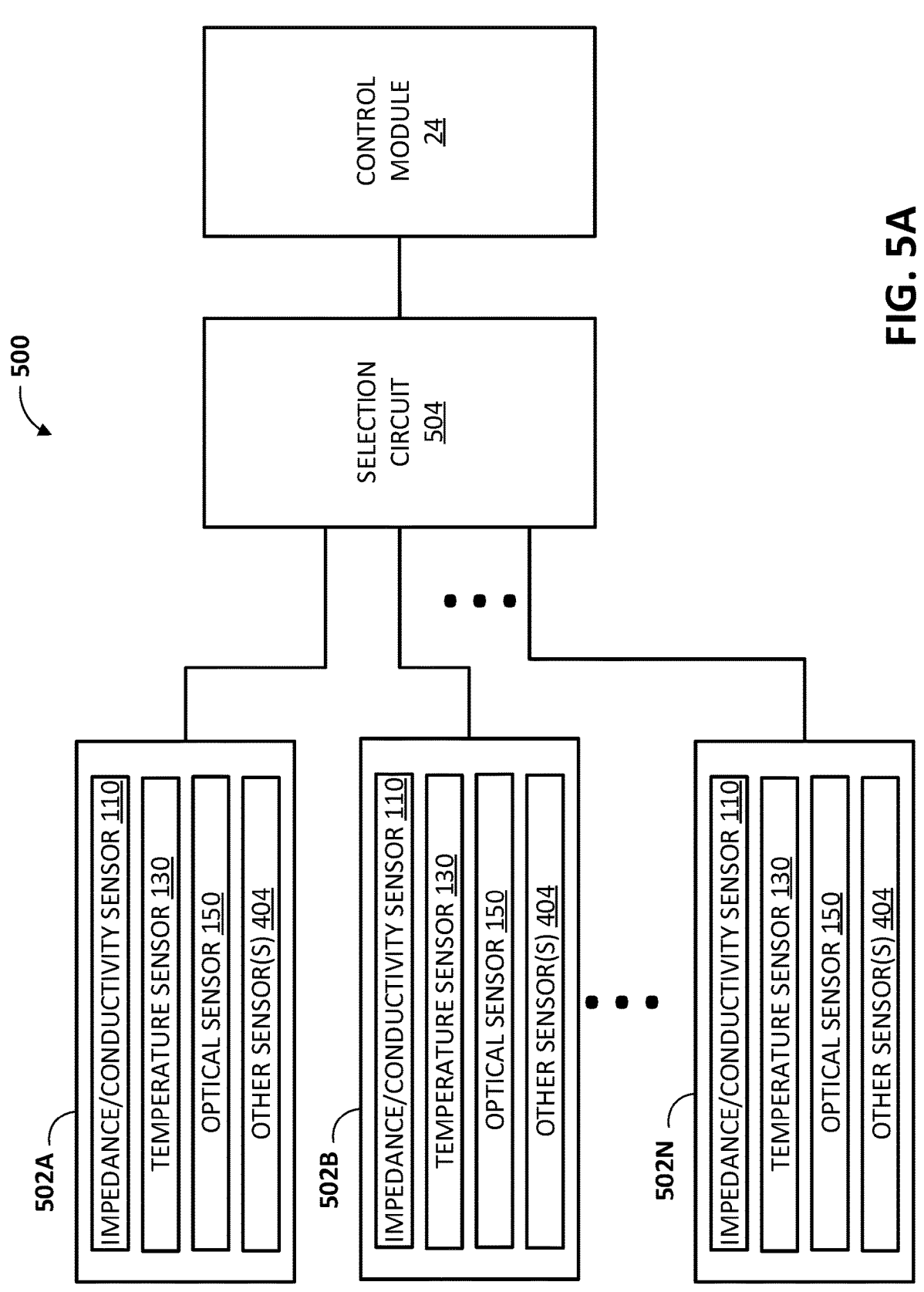
FIGS. 5A-5C illustrate wound monitoring or therapy apparatuses.

FIG. 5A illustrates a wound monitoring or therapy apparatus 500. The wound monitoring or therapy apparatus 500 can include a control module 24, a selection circuit 504, and a plurality of sensor circuits 502A, 5028, . . . , 502N (hereinafter individually or collectively referred to as sensor circuit 502). Further, although each of the sensor circuits 502 is depicted identically, it should be understood that one or more of the sensor circuits 502 may be configured differently. For simplicity, the sensor circuits 502 will be described generally. However, it should be understood that any description of a selection circuit 504 may apply to one or more of the sensor circuits 502 and may or may not apply to each of the sensor circuits 502.

The wound monitoring or therapy apparatus 500 can be used with any of the systems described herein, such as the wound monitoring or therapy systems 300 or 400. For example, in some cases, the wound monitoring or therapy apparatus 500 can further include one or more of a sensor enabled wound dressing 22 or a sensor integrated substrate 302, either of which can support of include one or more of the selection circuit 504, sensor circuits 502, or the like.

The sensor circuits 502 can include one or more sensors such as a temperature sensor 130, an optical sensor 150, an impedance/conductivity sensor 110, or one or more other sensors 404, such as an accelerometer, a motion sensor, a gyroscope, a pH sensor, a pressure sensor, or a perfusion sensor. In addition to or alternatively, the sensor circuits 502 can include one or more components for receiving or processing sensor signals from the one or more sensors. For example, the sensor circuits 502 can include one or more of an amplifier, a capacitor, a resistor, an inductor, a diode, or the like, which can filter, amplify, or otherwise process a sensor signal from the one or more sensors.

In some cases, the sensor circuit 502 can receive or process a plurality of sensor signals, where each sensor signals corresponds to a different measurement of one or more of the sensors. For example, a first sensor can be a temperature sensor and can provide a first signal. Furthermore, a second sensor can be a conductivity sensor and can provide a second signal. The sensor circuit 502 can receive or process the first and second signals to combine the first and second signals into a single signal, which can sometimes be referred to as a single output signal. As descried herein, the sensors can include any of various sensors, and one or more of the sensors can be positioned on a substrate that is configured to be in contact with a wound. Furthermore, in some cases, the sensor circuit 502 can combine or merge more than two sensor signals, such as three, four, or more sensor signals.

The selection circuit 504 can be electrically coupled to the control module 24 such that it can receive the single output signal from each of the plurality of sensor circuits 502. The selection circuit 504 can select or output one or more of the single output signals. For example, the selection circuit 504 can include one or more multiplexors, each multiplexor having multiple inputs (for instance, an input associated with each of the sensor circuits 502), a single output, and one or more select lines that can be used to select which input to send to the output. In some cases, the control module 24 can provide the selection circuit 504 with one or more signals for the select lines, which can be used by the selection circuit 504 to select which input line(s) to output. The selection circuit 504 can communicate one or more output signals to the control module 24, and such one or more signals can correspond to the output of the selection circuit 504. The selection circuit 504 can output the single output signal of a selected sensor circuit of the plurality of sensor circuits 502, for example, based on a selection signal received from the control module 24. The selection circuit can include one or more analog multiplexers.

The control module 24, for example a processor of control module 24, can be in electrical communication with the selection circuit 504. Furthermore, the control module 24 can communicate, to the selection circuit 504, which of the plurality of sensor circuits 502 to select. In some cases, because a particular sensor circuit 502 is associated with a particular sensor, the control module 24 can choose which sensor circuit 502 to select based at least in part on the sensor or sensors with which the selected sensor circuit 502 is associated.

The control module 24 can receive, from the selection circuit 504, the single output signal of the selected sensor circuit 502. Further, the control module 24 can extract, decompose, or otherwise identify each of the plurality of sensors signals associated with the single output signal of the selected sensor circuit. For example, a sensor input signal can correspond to a DC component or zero-frequency component of the single output signal, and a second sensor signal can correspond to a non-zero-frequency component of the single output signal, such as 1 kHz, 5 kHz, 10 kHz, 20 kHz, 50 kHz, 100 kHz, etc. Furthermore, in some examples, additional sensor input signals can correspond to other non-zero-frequency components of the single output signal.

In some cases, to extract, decompose, or otherwise identify each of the plurality of sensors signals associated with the single output signal, the control module 24 can demodulate the single output signal. In addition to or alternatively, to extract, decompose, or otherwise identify each of the plurality of sensors signals associated with the single output signal, the control module 24 can perform a Fourier transform or perform additional or alternative signal processing on the single output signal.

Figure 5B:
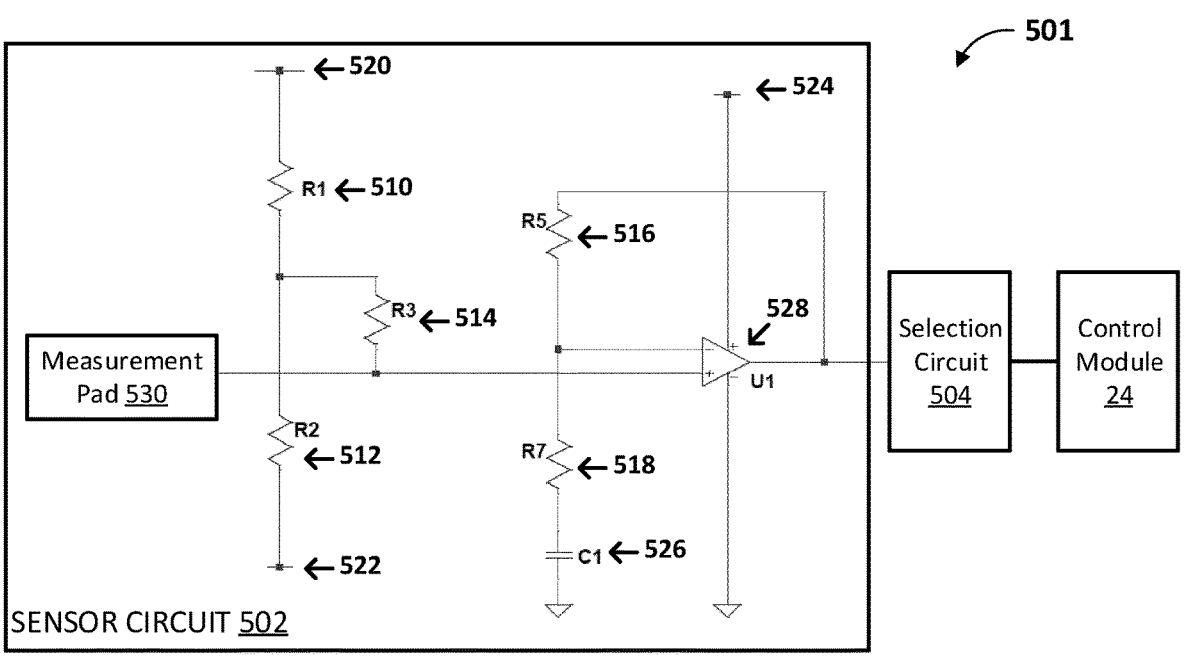

FIG. 5B illustrates a wound monitoring or therapy apparatus 501, which can be similar to the wound monitoring or therapy apparatus 500 of FIG. 5A. In this example, the sensor circuit 502 includes an impedance sensor paired with a temperature sensor. For example, resistor 512 can correspond to the temperature sensor (such as, a thermistor), whose resistance is dependent on temperature. Furthermore, a measurement pad 530 can correspond to a measurement from the impedance sensor. The measurement pad 530 can be similar to the measurement pad 110 described herein.

The sensor circuit 502 can include a plurality of resistors 510, 512, 514, 516, and 518, a capacitor 526, an amplifier 528, a measurement pad 530, a temperature sensor ground signal 522, a temperature sensor reference voltage 520, and a voltage source 524. In this example, the temperature measurement is effectively a DC measurement (zero-frequency component) of the voltage developed across the temperature sensor (resistor 512) while the impedance sensing is a non-zero frequency signal (for example, 50 kHz signal). In this example, the temperature reading is not likely to be influenced by the impedance signal.

The sensor circuit 502 can processes the sensor signals from the temperature sensor and the impedance sensor to generate a single output signal, which can be provided to the selection circuit 504. In some cases, because the temperature signal is combined with the impedance signal, such as used to provide the DC bias for the impedance signal, the number of dressing-to-controller connections 304 or other electrical connections can be reduced.

Figure 5C:
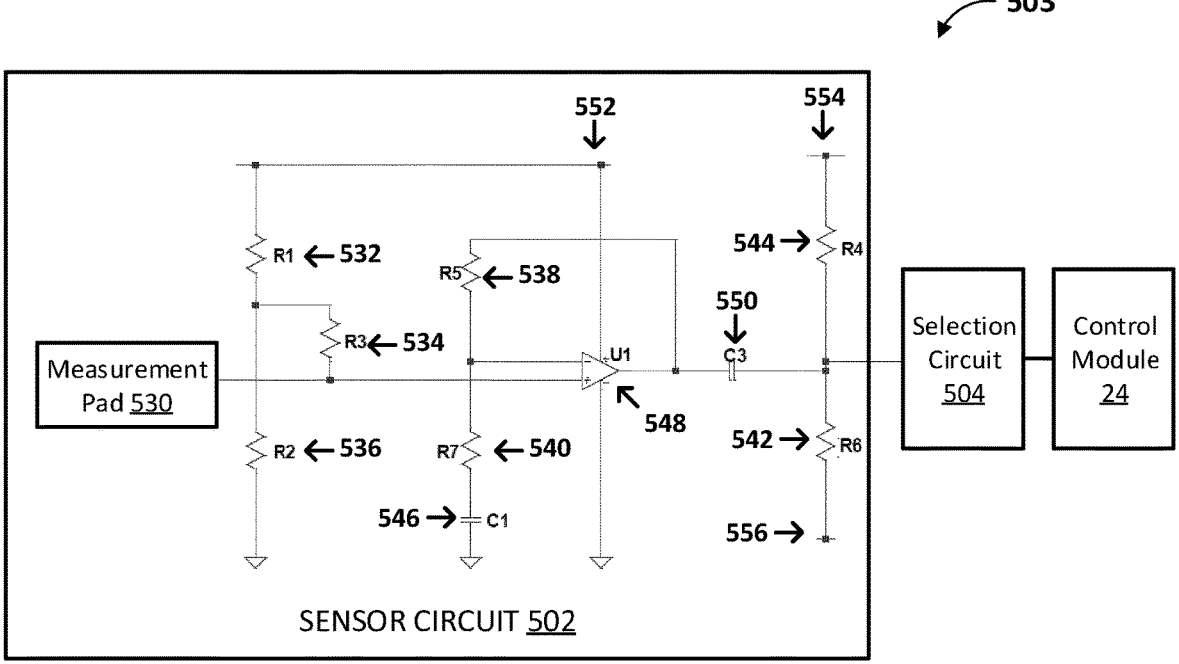

FIG. 5C illustrates a wound monitoring or therapy apparatus 503, which can be similar to the wound monitoring or therapy apparatus 500 of FIG. 5A. In this example, the sensor circuit 503 can include an impedance sensor paired with a temperature sensor. For example, resistor 542 can correspond to the temperature sensor (such as, a thermistor), whose resistance is dependent on temperature. Furthermore, the measurement pad 530 can correspond to a measurement from the impedance sensor.

The sensor circuit 503 includes a plurality of resistors 532, 534, 536, 538, 540, 542, and 544, capacitors 546 and 550, an amplifier 548, a measurement pad 530, a temperature sensor ground signal 556, a temperature sensor reference voltage 554, and a voltage source 552. In this example, the temperature measurement is effectively a DC measurement (zero-frequency component) of the voltage developed across the temperature sensor (resistor 542), while the impedance sensing is a non-zero frequency signal (for example, a 50 kHz signal).

The sensor circuit 503 can process the sensor signals from the temperature sensor and the conductivity sensor to generate a single output signal, which can be provided to the selection circuit 504. As described herein, the number of dressing-to-controller connections 304 or other electrical connections can be reduced.

In some cases, the selection circuit 504 can be connected to a controller, such as the control module 24, which can be connected to the control module 24. As described herein, the single output signal can be digitized by the controller. With this approach, the number of dressing-to-controller connections 304 can be reduced to 10 or the like.

In some cases, optical measurements can be combined into the signal output signal as described herein. For example, optical signal(s) can occupy lower frequency spectrum (such as, 1 kHz to 10 kHz) than the impedance signal(s).

Other Variations

In some cases, one or more electronic components can be positioned on the side of a substrate opposite the side that faces the wound. Systems and methods described herein are equally applicable to such substrates. Although certain embodiments described herein relate to wound dressings, systems and methods disclosed herein are not limited to wound dressings or medical applications. Systems and methods disclosed herein are generally applicable to electronic devices in general, such as electronic devices that can be worn by or applied to a user.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as controllers, processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately," "about," "generally," and "substantially" may refer to an amount that is within less than 10% of, within less than 5% of, within less than 1% of, within less than 0.1% of, and within less than 0.01% of the stated amount.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A wound monitoring and/or therapy apparatus comprising:
   a substrate configured to be positioned at least partially in a wound, the substrate supporting a plurality of sensors;
   a plurality of sensor circuitries positioned on the substrate, each sensor circuitry configured to process a plurality of input signals to generate a single output signal from the plurality of input signals, wherein the plurality of input signals corresponds to measurements from at least two sensors of the plurality of sensors, and wherein the at least two sensors are each of a different type;
   a selection circuitry positioned on the substrate and coupled to each sensor circuitry of the plurality of sensor circuitries, the selection circuitry configured to receive a plurality of single output signals from the plurality of sensor circuitries and output a selected single output signal of the plurality of single output signals; and
   a processing circuitry configured to be in electrical communication with the selection circuitry, the processing circuitry configured to:
      communicate, to the selection circuitry, an indication of a selected sensor circuitry of the plurality of sensor circuitries,
      receive, from the selection circuitry, a selected single output signal generated by the selected sensor circuitry, and
      separately extract each input signal of a plurality of input signals from the selected single output signal of the selected sensor circuitry.

2. The apparatus of claim 1, wherein the plurality of input signals from the selected single output signal comprises at least a first input signal and a second input signal, wherein the first input signal corresponds to a zero-frequency component of the selected single output signal, and wherein the second input signal corresponds to a non-zero-frequency component of the selected single output signal.

3. The apparatus of claim 2, wherein the non-zero-frequency component of the selected single output signal is a first non-zero-frequency component of the selected single output signal, and wherein the plurality of input signals further comprises a third input signal, the third input signal corresponding to a second non-zero-frequency component of the selected single output signal that is different from the first non-zero-frequency component of the selected single output signal.

4. The apparatus of claim 3, wherein the first non-zero-frequency component of the selected single output signal corresponds to a frequency of 50 kHz.

5. The apparatus of claim 4, wherein the second non-zero-frequency component of the selected single output signal corresponds to a frequency between 1 kHz and approximately 10 kHz.

6. The apparatus of claim 1, wherein the plurality of input signals comprises at least a first input signal and a second input signal, and wherein the first input signal corresponds to a DC component of the selected single output signal.

7. The apparatus of claim 6, wherein the first input signal corresponds to measurements from a first sensor of the plurality of sensors and the second input signal corresponds to a measurement from a second sensor of the plurality of sensors.

8. The apparatus of claim 7, wherein each of the first and second sensors comprises one of a temperature sensor, an optical sensor, an accelerometer, a motion sensor, a gyroscope, an impedance sensor, a conductivity sensor, a pH sensor, a pressure sensor, or a perfusion sensor, and wherein the first and second sensors are of a different type.

9. The apparatus of claim 7, wherein the first sensor is a temperature sensor and the second sensor is an impedance sensor.

10. The apparatus of claim 1, wherein the processing circuitry is configured to separately extract each of the plurality of input signals from the selected single output signal of the selected sensor circuitry by being further configured to:

determine a first input signal of the plurality of input signals based at least in part on a zero-frequency component of the selected single output signal of the selected sensor circuitry; and determine a second input signal of the plurality of input signals based at least in part on a non-zero-frequency component of the selected single output signal of the selected sensor circuitry.

11. A method of operating a wound monitoring and/or therapy apparatus, the method comprising:

by a processing circuitry, communicating to a selection circuitry positioned on a substrate and coupled to each sensor circuitry of a plurality of sensor circuitries an indication of a selected sensor circuitry of the plurality of sensor circuitries, wherein:

the substrate is configured to be positioned at least partially in a wound and the substrate supports a plurality of sensors;

the plurality of sensor circuitries is positioned on the substrate and configured to process a plurality of input signals to generate a single output signal from the plurality of input signals, the plurality of input signals corresponding to measurements from at least two sensors of the plurality of sensors, the at least two sensors each being of a different type; and the selection circuitry is configured to receive a plurality of single output signals from the plurality of sensor circuitries and output a selected single output signal of the plurality of single output signals;

by the processing circuitry, receiving from the selection circuitry, a selected single output signal generated by the selected sensor circuitry; and by the processing circuitry, separately extracting each input signal of a plurality of input signals from the selected single output signal of the selected sensor circuitry.

12. The method of claim 11, wherein the plurality of input signals from the selected single output signal comprises at least a first input signal and a second input signal, wherein the first input signal corresponds to a zero-frequency component of the selected single output signal, and wherein the second input signal corresponds to a non-zero-frequency component of the selected single output signal.

13. The method of claim 12, wherein the non-zero-frequency component of the selected single output signal is a first non-zero-frequency component of the selected single output signal, and wherein the plurality of input signals further comprises a third input signal, the third input signal corresponding to a second non-zero-frequency component of the selected single output signal that is different from the first non-zero-frequency component of the selected single output signal.

14. The method of claim 13, wherein the first non-zero-frequency component of the selected single output signal corresponds to a frequency of approximately 50 KHz.

15. The method of claim 14, wherein the second non-zero-frequency component of the selected single output signal corresponds to a frequency between approximately 1 kHz and approximately 10 kHz.

16. The method of claim 11, wherein the plurality of input signals comprises at least a first input signal and a second input signal, and wherein the first input signal corresponds to a DC component of the selected single output signal.

17. The method of claim 16, wherein the first input signal corresponds to measurements from a first sensor of the plurality of sensors and the second input signal corresponds to a measurement from a second sensor of the plurality of sensors.

18. The method of claim 17, wherein each of the first and second sensors comprises one of a temperature sensor, an optical sensor, an accelerometer, a motion sensor, a gyroscope, an impedance sensor, a conductivity sensor, a pH sensor, a pressure sensor, or a perfusion sensor, and wherein the first and second sensors are of a different type.

19. The method of claim 17, wherein the first sensor is a temperature sensor and the second sensor is an impedance sensor.

20. The method of claim 11, further comprising separately extracting each of the plurality of input signals from the selected single output signal of the selected sensor circuitry by:

determining a first input signal of the plurality of input signals based at least in part on a zero-frequency component of the selected single output signal of the selected sensor circuitry; and determining a second input signal of the plurality of input signals based at least in part on a non-zero-frequency component of the selected single output signal of the selected sensor circuitry.

* * * * *